(12) United States Patent
Scoglio et al.

(10) Patent No.: US 8,337,858 B2
(45) Date of Patent: Dec. 25, 2012

(54) EXTRACTS OF APHANIZOMENON FLOS AQUAE AND NUTRITIONAL, COSMETIC AND PHARMACEUTICAL COMPOSITIONS CONTAINING THE SAME

(75) Inventors: Stefano Scoglio, Urbino (IT); Franco Canestrari, Urbino (IT); Serena Benedetti, Urbino (IT); Leilo Zolla, Urbino (IT)

(73) Assignee: Nutratec S.R.L., Urbino (IT)

( * ) Notice: Subject to any disclaimer, the term of this patent is extended or adjusted under 35 U.S.C. 154(b) by 206 days.

(21) Appl. No.: 12/306,478

(22) PCT Filed: Jun. 27, 2007

(86) PCT No.: PCT/EP2007/005623
§ 371 (c)(1),
(2), (4) Date: Oct. 8, 2009

(87) PCT Pub. No.: WO2008/000431
PCT Pub. Date: Jan. 3, 2008

(65) Prior Publication Data
US 2010/0021493 A1    Jan. 28, 2010

Related U.S. Application Data

(60) Provisional application No. 60/816,954, filed on Jun. 27, 2006.

(51) Int. Cl.
*A61K 36/02* (2006.01)
(52) U.S. Cl. ................................ 424/195.17
(58) Field of Classification Search ............. None
See application file for complete search history.

(56) References Cited

U.S. PATENT DOCUMENTS 6,787,147 B1 * 9/2004 Huner et al. ............. 424/401
7,651,690 B2 * 1/2010 Jensen et al. ........... 424/195.17
7,846,452 B2 * 12/2010 Pasco et al. ............ 424/195.17

FOREIGN PATENT DOCUMENTS

| FR | 2 850 277 | | 7/2004 |
| WO | WO 02/04000 | * | 1/2002 |
| WO | WO 02/04000 A1 | | 1/2002 |
| WO | WO 2007/002570 A1 | | 1/2007 |

OTHER PUBLICATIONS

Ikawa (Environmental Science Research (1981), vol. 20, (Water Environ.: Algal Toxins Health), pp. 415-425).*
Ostensvik (Journal of Applied Microbiology (1998), vol. 64, pp. 1117-1124).*
Pugh N et al; "Characterization of Human Monocyte Activiation by a Water Soluble Preparation of Aphanizomenon Flos-aquae", Phytomedicine, Gustav Fischer Verlag, Stuttgart, DE, 2001, pp. 445-453, vol. 8.
Torres Avital et al; "Porphyra-334, A Potential Natural Source for UVA Protective Sunscreens", Photochemical and Photobiological Sciences, Royal Society of Chemistry, Cambridge, GB, Apr. 2006, pp. 432-435.
Benedetti S et al; "Antioxidant Properties of a Novel Phycocyanin Extract from the Blue-Green Alga Aphanizomenon Flos-Aquae", Life Sciences, Pergamon Press, Oxford, GB, Sep. 24, 2004, pp. 2353-2362, vol. 75 No. 19.
Benedetti et al; "Purification and Characterization of Phycocyanin from the Blue-Green Alga Aphanizomenon Flos-Aquae", Journal of Chromatography B: Biomedical Sciences & Applications, Elsevier, Amsterdam, NL, Mar. 20, 2006, pp. 12-18, vol. 833 No. 1.
Carmichael Wayne W et al; "Harvesting of Aphanizomenon Flos-Aquae Ralfs ex Born. And Flah. var. Flos-Aquae (Cyanobacteria) from Klamath Lake for Human Dietary Use" Journal of Applied Phycology, Dec. 2000 vol. 12 No. 6.

* cited by examiner

*Primary Examiner* — Susan Hoffman
(74) *Attorney, Agent, or Firm* — Arent Fox LLP

(57) ABSTRACT

The invention provides extracts of the microalga *Aphanizomenon Flos Aquae Aquae* Ralfs ex Born. & Flah. Var. *flos aquae* (AFA Klamath) and biologically active components thereof, in particular AFA-phycocyanins, determined as the complex c-phycopcyanin/phycoerythrocyanin (including the chromophore phycoviolobilin), AFA-phytochrome and mycosporine-like aminoacids (MAAs), nutritional, cosmetic and pharmaceutical compositions containing the same, for use in the prophylaxis or treatment of diseases, disturbances or conditions involving acute or chronic inflammation and oxidative degeneration of body cells or tissues or uncontrolled cell proliferation.

10 Claims, 37 Drawing Sheets

SYNECHOCYSTIS sp. 6803

APHANIZOMENON FLOS AQUA

FIGURE 4

| Photoprotective compounds | $\lambda_{max}$ (nm) | Molecular structure | Extinction coefficient ($\epsilon$) |
|---|---|---|---|
| Mycosporine-glycine | 310 | 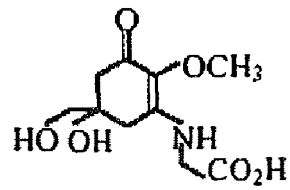 | 28100 |
| Palythine | 320 | 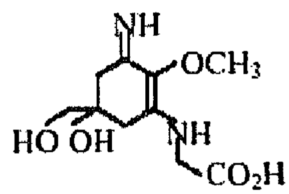 | 36200 |
| Asterina-330 | 330 | 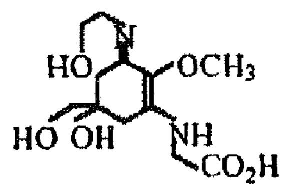 | 43500 |
| Palythinol | 332 | 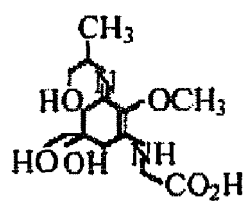 | 43500 |
| Porphyra-334 | 334 | 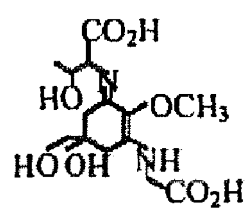 | 42300 |
| Shinorine | 334 | 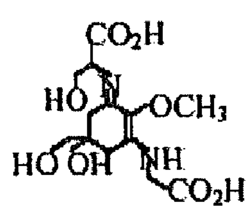 | 44700 |
| Palythene | 360 | | 50000 |

# EXTRACTS OF APHANIZOMENON FLOS AQUAE AND NUTRITIONAL, COSMETIC AND PHARMACEUTICAL COMPOSITIONS CONTAINING THE SAME

CROSS-REFERENCE TO RELATED APPLICATION

This application is a National Stage entry of International Application No. PCT/EP2007/005623, filed Jun. 27, 2007, which in turn claims priority from U.S. Provisional Application No. 60/816,594 filed Jun. 27, 2006, the entire specification claims and drawings of which are incorporated herewith by reference.

The present invention provides extracts of the microalga *Aphanizomenon Flos Aquae Aquae* Ralfs ex Born. & Flah. Var. *flos aquae* (AFA Klamath) and the biologically active components thereof endowed with antioxidant, antiinflammatory and antitumor properties. Furthermore the invention provides nutritional, cosmetic and pharmaceutical compositions containing effective amounts of the extract or the active components thereof, in particular AFA-phycocyanin, with its C-phycocyanin/phycoerythrocyanin complex, AFA-phytochrome and mycosporine-like aminoacids (MAAs), alone or in combination with cofactors contained in the algae, for use in the prophylaxis or treatment of diseases, disturbances or conditions involving acute or chronic inflammation and oxidative degeneration of body cells or tissues or uncontrolled cell proliferation.

BACKGROUND OF THE INVENTION

*Aphanizomenon Flos Aquae* (AFA), which is one of the many types of blue-green algae, is found in abundance in Upper Klamath Lake in southern Oregon. It is one of the few edible microalgae, and it differs from other microalgae grown in ponds, such as *Spirulina* and *Chlorella*, insofar as it grows wild in an optimal environment which allows it to develop a truly remarkable nutritional profile, including a wide range of vitamins and organic minerals, proteins and aminoacids, Omega 3 fatty acids. It is also known to contain a certain number of nutrients endowed with antioxidant properties, such as chlorophyll and carotenes. Various studies in the last few years have shown significant antioxidant and antiinflammatory properties possessed by the phycocyanins of the blue-green microalga *Spirulina;* more recently, the in vitro antioxidant properties of a crude extract of AFA have been reported (Benedetti S., Scoglio S., Canestrari F., et al., Antioxidant properties of a novel phycocyanin extract from the blue-green alga Aphanizomenon Flos Aquae, in Life Sciences, 75 (2004): 2353-2362).

DISCLOSURE OF THE INVENTION

The invention provides extracts of Klamath microalgae (*Aphanizomenon Flos Aquae Aquae* Ralfs ex Born. & Flah. Var. *flos aquae*) which concentrate the active components of the alga, namely:
a) a specific phycobiliprotein complex, unique to AFA algae, which contains i) a phycobilisome comprising C-phycocyanin (C-PC) and phycoerythrocyanin (PEC)—hereafter indicated as "AFA-phycocyanins"—and including its specific chromophore phycoviolobilin; ii) an AFA-specific phytochrome (herein indicated as AFA-phytochrome");
b) MAAs (mycosporine-like aminoacids), chlorophyll and carotenes.

The extraction process makes use of centrifugation and size exclusion separation techniques which can be modulated to modify the concentration of the different components. To guarantee adequate concentration of different components, the first phase is preparing an aqueous extract (herein indicated as Basic Extract), according to the following steps:
a) freezing the freshly harvested AFA alga and thawing it, or, if the starting material is dried AFA powder, sonicating the water-diluted AFA powder, to disrupt the cells;
b) centrifuging the product of step a) to separate the supernatant (retaining most of the cytoplasmatic fraction) from the precipitate (retaining most of the cell wall fraction);
c) collecting the supernatant containing the water-soluble components (Basic Extract).

It is possible to further concentrate the water-soluble fractions by passing the supernatant through an ultra-filtration membrane. In particular, to prepare extracts concentrated in water-soluble components, the primary aqueous extract described above (Basic Extract) is subjected to size-exclusion ultrafiltration, preferably by using a membrane with a molecular weight cut-off of 30 kDa, whereby a retentate (indicated as Extract B) and a filtrate are obtained. Extract B contains a higher concentration of AFA-phycocyanins (C-PC+PEC) and of the AFA-phytochrome. Interestingly, even though MAAs have a molecular weight well below the cut-off size employed, the retentate also increases the concentration of MAAs. The filtrate, on the other hand, has a higher concentration of carotenes, chlorophyll and essential fatty acids.

The lipophilic components of the extract are mainly represented by carotenes, chlorophyll, and alpha-linolenic acid (18:3n-3), all of which are present in relatively high amounts in AFA algae. These components are in part retained in the supernatant (Basic Extract), but for the most part they are present in the precipitate resulting from centrifugation at step b) above. This precipitate can be then subjected to a further process of extraction directed at concentrating the above mentioned liposoluble substances. The concentration of the liposoluble substances is preferably obtained through an ethanol based extraction, according to the following steps:
a) suspending the dried precipitate in a solution of 100% ethanol, homogenizing and maintaining the homogenate under constant stirring for 24 h at room temperature in the dark;
b) centrifuging the resulting suspension at 3000 rpm for 5' at 4° C.;
c) collecting the supernatant;
d) optionally, subjecting the pellet to a second ethanol extraction according to steps a) through c);
e) drying the supernatant to obtain a lipid-soluble concentrate (Extract C).

The thus obtained liposoluble component-enriched fraction can then be added to Basic Extract or to the filtrate from the ultrafiltration, to obtain the highest possible concentration of liposoluble substances that enhance the effects of the biologically-active substances already present in the extracts.

The extracts according to the invention can be provided in the form of nutritional supplements, pharmaceutical and/or cosmetic products. The Basic Extract is generally preferred as it retains very significant antioxidant and anti-inflammatory properties.

The components that retain or enhance the antioxidant properties of the extract have been isolated and physico-chemically characterized. The specific type of AFA-phycocyanin (C-PC/PEC); the chromophore phycoviolobilin (PVB); the specific AFA-phytochrome; the mycosporine-like amino acids (MAAs) porphyra and shinorine, resulted the most active, singularly or in various combinations, and their antioxidant activity was further increased by other components such as chlorophyll, beta-carotene, pro-vitamin A carotenoids, xantophyllic carotenes such as canthaxanthin, vitamins and minerals. In addition to their demonstrated antioxidant activity, both the Basic Extract and the purified AFA-phycocyanins were found to significantly inhibit the cycloxygenase-2 (COX-2) enzyme; this property was then confirmed for the Basic Extract which, by including both AFA-PC and other antinflammatory molecules, proved able to prevent and/or suppress inflammation in an in vivo animal model. Furthermore, tested on a tumor cell line, the AFA-phycocyanin showed to possess high antiproliferative activity.

Accordingly, the invention further includes a nutritional, cosmetic or pharmaceutical composition containing, as the active ingredient, an extract of Klamath microalgae or an isolated and purified active component thereof, in particular: a) the specific type of AFA-phycocyanins (C-PC/PEC), as present in AFA or in any other microalgae b) the PEC; c) the phycoviolobilin (PVB); d) the AFA-phytochrome; e) the mycosporine-like amino acids (MAAs) porphyra and shinorine, as present in AFA, or from any other algal source; optionally in combination with co-factors or coadjuvants selected from chlorophyll, beta-carotene, pro-vitamin A carotenoids, xantophyllic carotenes, canthaxanthin, vitamins and minerals, and optionally in combination with nutritionally, cosmetically or pharmaceutically acceptable vehicles or excipients. To prepare the compositions according to the invention, the different liquid extracts mentioned above can be either used as such or can be dried through methodologies such as freeze-drying, spray-drying, and others.

In a preferred embodiment, the nutritional compositions are dietary supplements in the form of tablets, capsules, beverages, which are useful for increasing or supporting the natural defenses against pathogens, for scavenging oxidant species produced by metabolic, inflammatory and aging processes. In another preferred embodiment, the cosmetic compositions are in the form of topical preparations, such as emulsions, gels, lotions, powders, eyewashes, particularly ointments or creams, for use in the prevention or treatment of dermatological or age-related affections, and as photo-protective agents to prevent skin aging and photo-oxidative degeneration of skin and hair.

In a yet further preferred embodiment, the pharmaceutical compositions are in the form of tablets, capsules, sachets, syrups, suppositories, vials and ointments and can be used for the prevention or treatment of free-radical mediated pathologies, inflammation or neoplasias.

BRIEF DESCRIPTION OF THE DRAWINGS

FIG. 4 shows the structures of mycosporine-like amino acids (MAAs).

DETAILED DESCRIPTION OF THE INVENTION

Structural Determination and Specific Characteristics of the AFA Alga's Phycobilisomes (AFA-Phycocyanins)

In the intact cyanobacterial cell phycocyanins (PC) are present inside the phycobilisome in the functional form $(..)_6$ (1). Following the break-up of the cell, the protein can be found in different aggregation states (monomers, dimers, trimers, hexamers) according to the organism analyzed. In the case of Klamath AFA algae, the electrophoretic analysis of the PC, both as contained in the AFA extracts and as purified from the extract itself, has shown that the protein is found for the most part in its trimeric form $(..)_3$, with a total molecular weight of 121000. A monomer .. weighs approximately 40000 (18500 subunit .+21900 subunit .). The majority of the studies on the purified PC from *Spirulina* indicate instead that the protein is found in *Spirulina* in the monomeric form .. with a molecular weight of approximately 37500, thus showing a different aggregation state relative to the purified PC from AFA.

The chromatographic analysis of the AFA's phycobilosomes has also shown that, as in other cyanobacterial species, the . subunit of PC binds a prosthetic group, while the . subunit binds two. The prosthetic group or chromophore is called phycocyanobilin (PCB) and is responsible both for the blue color of the protein and for its antioxidant power (2).

A fundamental difference between AFA and *Spirulina* rests on the different structure of the phycobilisome. As opposed to *Spirulina*, the phycobilisome of AFA Klamath does not contain the pigment allo-phycocyanin, but only the pigment c-phycocyanin bound to a structural component which is missing in *Spirulina*, namely phycoerythrocyanin (PEC). PEC is a photosynthetic pigment which has so far been identified only in a limited number of cyanobacterial species (3). PEC has a chemical structure very similar to that of PC, being composed by the two subunits . e . which associate to form monomers and trimers. Nevertheless, while every monomer of PC binds 3 molecules of PCB, PEC possesses the unique characteristic of binding two molecules of PCB to the subunit . and one molecule of phycoviolobilin (PVB) to the . subunit, which is responsible of the purple color of the pigment.

The phycobilisome of Klamath algae is peculiarly constituted by the union of c-phycocyanin and phycoerithrocyanin, and this different qualitative structure of the phycobilisome of AFA Klamath algae adds a further decisive factor distinguishing AFA from *Spirulina* and other blue-green algae.

Figure 1:
FIG. 1 shows a comparison of the components of the cellular lysate of AFA Klamath with the components of the cellular lysate of Synechocystis PCC 6803.
Figure 1:
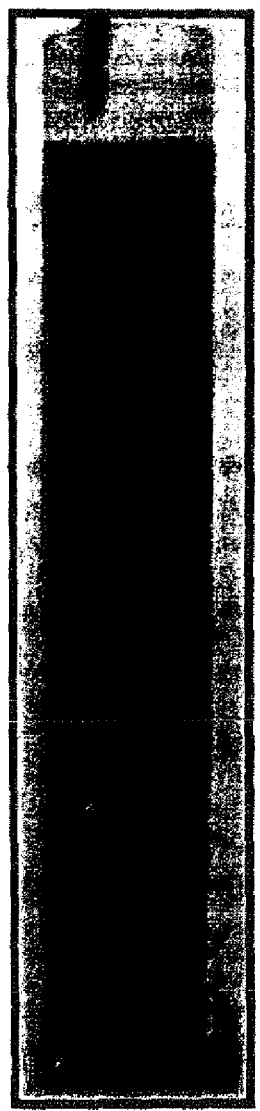
Figure 1:

FIG. 1 compares the components of the cellular lysate of AFA with those of another well known cyanobacterium, Synechocystis PCC 6803. In both cyanobacteria it is possible to see the blue band representing the phycobilisome, but in AFA algae the phycobilisome presents a lower molecular mass, confirming that, as opposed to common microalgae such as *Spirulina*, in the AFA phycobilisome only phycocyanins, but not allo-phycocyanins, are present. Furthermore, FIG. 1 shows that in AFA is also present a light purple band (shown by the arrow) which is typical of phycoerythrocyanins, thus proving their presence in the phycobilisome of Klamath algae.

Each blue band has been further analyzed through HPLC connected to mass spectrometer (RP-HPLC-ESI-MS). Thanks to the different retention times, the proteins of the phycobilisome have been separated and identified based on their molecular mass. The results obtained are shown in the following tables. First it can be observed that while in Synechocystis (Table 1) both phycocyanin (cpcA at 28.2 min and cpcB at 28.9 min) and allo-phycocyanin (apcA at 30.7 min and apcB at 31.2 min) are present, in AFA (Table 2) only phycocyanin (cpcA at 28.8 min and cpcB at 30.0 min) is present. Secondly, in AFA a protein with molecular mass of 19469 has been identified which is not present in Synechocystis and which corresponds to the beta subunit of the phycoerythrocyanin with two bilins attached (pecB at 25.0 min).

TABLE 1 proteins present in the phycobilisome of *Synechocystis*.

| Retention time (min) | Measured molecular mass | Expected molecular mass | Protein [homologous organism] | NCBI Number of access |
|---|---|---|---|---|
| 14.5 | 9322 | 9322 | cpcD | gi\|16329820 |
| 22.6 | 32505 | 32520 | cpcC | gi\|16329821 |
|  | 32388 | 30797 | cpcC | gi\|16329822 |
| 24.6 | 28770 | 27392 | cpcG | gi\|16329710 |
| 24.8 | 28885 | 28522 | cpcG | gi\|16332194 |
| 28.2 | 18173 | 17586 | cpcA (sub. phycocyanin) | gi\|2493297 |
| 28.9 | 19313 | 18126 | cpcB (sub. phycocyanin) | gi\|2493300 |
| 30.7 | 17866 | 17280 | apcA (sub. allophycocyanin) | gi\|266765 |
| 31.2 | 17816 | 17215 | apcB (sub. allophycocyanin) | gi\|266766 |

TABLE 2 proteins present in the phycobilisome of AFA Klamath algae

| Retention time (min) | Measured molecular mass | Expected molecular mass | Protein [homologous organism] | NCBI Number of access |
|---|---|---|---|---|
| 15.2 | 9031 | 8925 | hypothetical protein Avar03000795 [*Anabaena variabilis* ATCC 29413] | gi\|45510540 |
|  |  | 8895 | cpcD [*Nostoc* sp. PCC 7120] | gi\|131740 |
| 25.0 | 19469 19308 | 18284 | pecB: phycoerythrocyanin beta chain [*Nostoc* sp. PCC 7120] | gi\|548504 |
|  |  | 18370 | hypothetical protein Avar03000787 (pecB) [*Anabaena variabilis* ATCC 29413] | gi\|45510532 |

TABLE 2-continued proteins present in the phycobilisome of AFA Klamath algae

| Retention time (min) | Measured molecular mass | Expected molecular mass | Protein [homologous organism] | NCBI Number of access |
|---|---|---|---|---|
| 26.4 | 31044 | 32078 | cpcC [Nostoc sp. PCC 7120] | gi|20141679 |
| | | 32219 | hypothetical protein Avar03000794 (rod linker Mw 32000) [Anabaena variabilis ATCC 29413] | gi|45510539 |
| | | 31295 | pecC [Nostoc sp. PCC 7120] | gi|464511 |
| | | 31304 | hypothetical protein Avar03000789 (pecC) [Anabaena variabilis ATCC 29413] | gi|45510534 |
| | 30124 | 29333 | hypothetical protein Avar03000801 (cpcG4) [Anabaena variabilis ATCC 29413] | gi|46135436 |
| 26.8 | 26119 | 28637 | hypothetical protein Avar03000799 (cpcG2) [Anabaena variabilis ATCC 29413] | gi|45510544 |
| 27.8 | 10994 | 10986 | fdxH2: ferredoxin vegetative [Anabaena variabilis] | gi|1169673 |
| 28.8 | 17714 | 17457 | cpcA [Nostoc sp. PCC 7120] | gi|9957319 |
| 30.0 | 19222 | 18332 | cpcB [Nostoc sp. PCC 7120] | gi|38894 |

This unique structure is an important element to explain the stronger antioxidant and antinflammatory action of the AFA algae's extract concentrating its phycocyanins, and most of all it is essential to explain why the purified AFA-phycocyanin resulted more powerful than other PC such as the one from *Spirulina* (as shown by both antioxidant and antinflammatory tests, see below). The binding between C-PC and PEC in AFA phycobilisome is so strong that cannot be broken by known purification methodologies (see below). Hence, the purified AFA-PC should be intended as the purified AFA-phycobilisome, constituted by the complex C-PC/PEC. For sake of simplicity, though, this complex is indicated as "AFA-PC" or PC.

Figure 2:
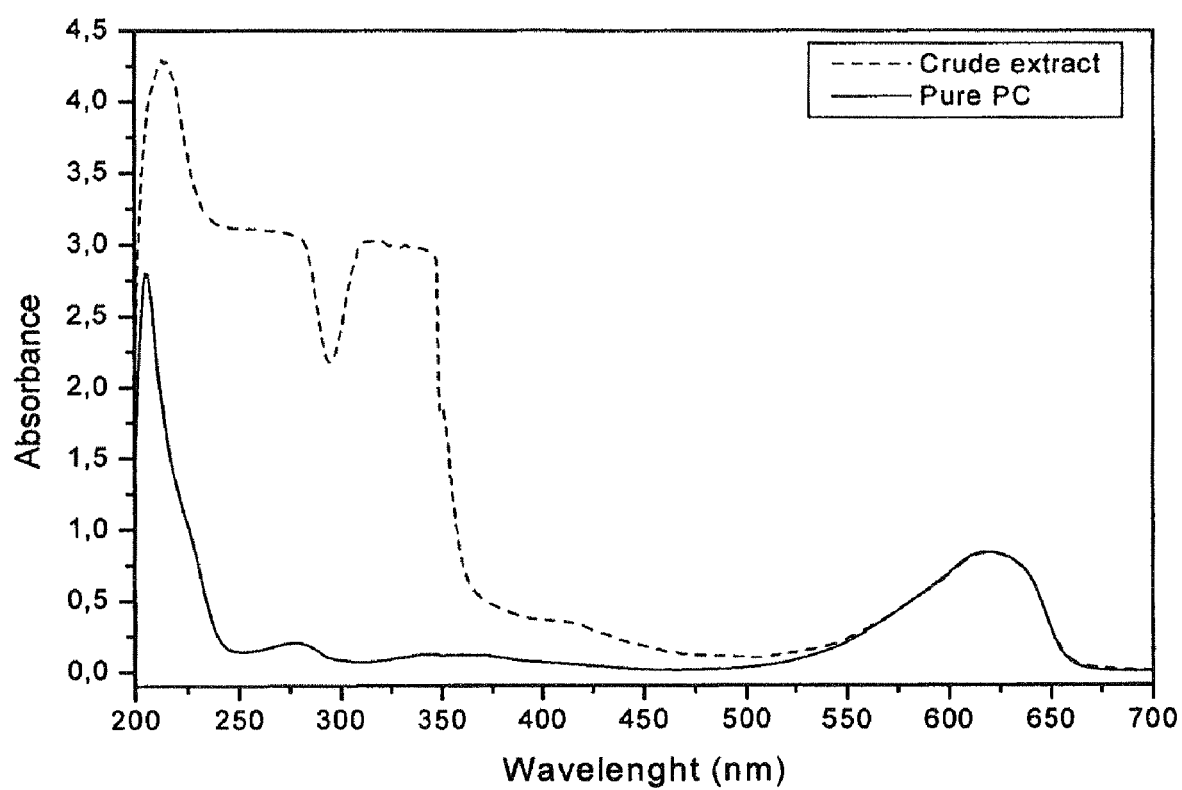
FIG. 2 shows the spectrophotometric graphic of the extract resulting from the purification of AFA-PC and its chromophore, PCB.

Purification Methodologies (FIG. 2)

AFA-PC and its chromophore PCB have been purified starting from the Basic Extract. PC was purified from the dried AFA extract as follows:
suspend 500 mg of extract in 50 ml of 100 mM Na-phosphate buffer pH 7.4;
centrifuge at 2500 rpm for 10' at 4° C.;
collect the supernatant and add solid ammonium sulfate to a 50% saturation;
precipitate the proteins for 60 min at 4° C. while keeping the sample in agitation;
centrifuge at 10000 rpm for 30 min at 4° C.;
discard the clear colorless supernatant and resuspend the blue precipitate in a small volume of 5mM Na-phosphate buffer pH 7.4;
dialyze overnight at 4 .C against the same buffer;
place the dialyzed PC in a 2.5×25 cm hydroxyapatite column (Bio-Rad Laboratories, CA, USA) balanced with 5 mM Na-phosphate buffer pH 7.4;
elute the sample with Na-phosphate buffer pH 7.0 of increasing ionic strength (from 5 to 150 mM);
collect the fractions and read the absorbance at 620 nm and 280 nm with the spectrophotometer;
pool the fractions in which $Abs_{620}/Abs_{280}>4$ (index of pure PC);
precipitate the PC with ammonium sulfate at 50% saturation for 1 hour at 4°;
centrifuge at 10000 rpm for 30' at 4° C.;
discard the supernatant and suspend again the PC in a 150 mM of Na-phosphate buffer pH 7.4;
dialyze against the same buffer at 4° C.;
transfer the purified PC in a flask and store in darkness at +4° C. or −20° C.

FIG. 2 shows the spectrophotometric graphic of the extract resulting from the purification. It can be seen that the purified PC is indeed the whole phycobilisome containing the two subunits C-PC and PEC. In fact, it is known that the absorption maximum of C-PC is 620 nm, which in the spectrometry of FIG. 2 represents the top of the peak. It is also known that the absorption maximum of PEC is 566 nm for the .-subunit (phycoviolobilin) and respectively 593 nm and 639 nm for the two PCBs of the .-subunit. All three values are indeed included in the bell-shaped peak constituting the spectrophotometric pattern of purified PC. Considering the strong link between C-PC and PEC in AFA algae, i C-PC as well as PEC are necessarily present in the purified PC extract. This means that the PC from AFA is significantly different, both structurally and functionally, from the PCs of other cyanobacteria, including the one from *Spirulina*, on which most studies have been done. In particular this difference consists in that the AFA PC has one part, namely C-PC, in common with PCs from other sources and one portion, the PEC component, which is different, so that its properties, associated to the complex C-PC/PEC, are novel and exclusively attributable to AFA (and similar C-PC/PEC complexes from other microalgae).

Quantification of AFA-Phycocyanin

To measure the molar concentration of the pur PC we used the coefficient of molar extinction . at 620 nm, which for the trimeric form $(..)_3$ is equal to 770000 $M^{-1}$ $cm^{-1}$. This means that a solution of 1 M of PC at 620 nm has an absorption value of 770000.

To measure the concentration of PC in the extracts we used the coefficient of specific extinction $E^{1\%}$ at 620 nm of 70 1 $g^{-1}$ $cm^{-1}$. This means that a solution containing 1% of PC (that is 1 g/100 ml) at 620 nm absorbs 70. Based on these calculations, the average content of PC in the Basic Extract is equal to 80-100 mg/g DW (8-10% DW); whereas the average content of PC in the Extract B is approximately 360 mg/g DW (36% DW).

Figure 3:
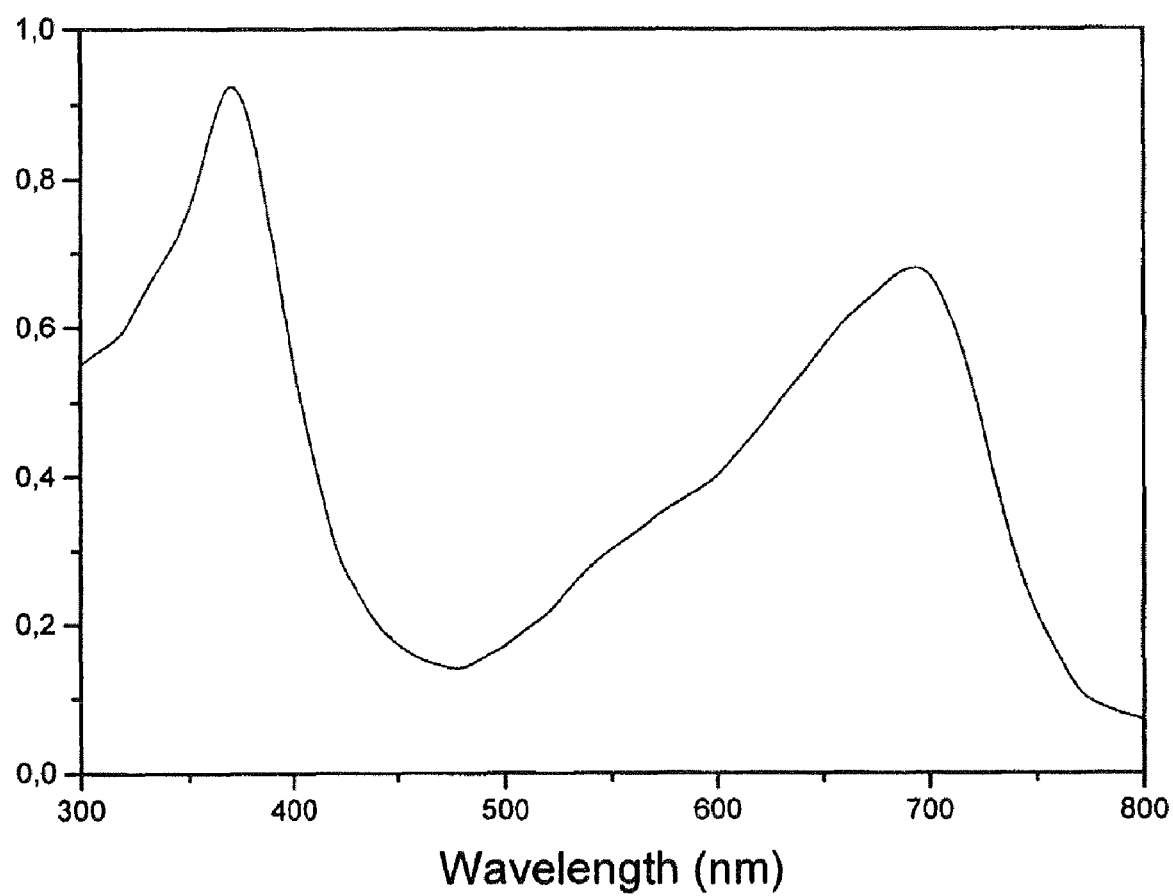
FIG. 3 shows a spectrophotometric scan of purified PCB indicating two peaks of absorption, 370 nm and 690 nm.

Purification of the PCB Chromophore (FIG. 3)

Suspend 500 mg of extract in 50 ml of distilled $H_2O$.
Centrifuge at 2500 rpm for 10' at 4° C.
Decant the deep blue supernatant and precipitate the PC with trichloroacetic acid at 1%.
Incubate for 1 h in the dark at 4° C., while agitating.
Centrifuge at 10000 rpm for 30' at 4° C.
Gather the pellet containing PC and wash 3 times with methanol.
Resuspend the pellet in 10 ml of methanol containing 1 mg/ml of $HgCl_2$.
Incubate for 20 h at 42° C. in darkness to release the PCB from PC.
Centrifuge at 2500 rpm for 10' to remove the proteins.
Add to the supernatant containing PCB .-mercaptoethanol (1 μl/ml) to precipitate the $HgCl_2$.
Incubate at −20° C. for 24 h.

Centrifuge at 10000 rpm for 30' at 4° C. to remove the white precipitate.

Add to the supernatant 10 ml of methylene chloride/butanol (2:1, v/v).

Wash with 20 ml of distilled $H_2O$ and centrifuge at 3000 rpm for 10'.

Remove the upper phase, collect the lower part containing PCB.

Wash the PCB in 15 ml $H_2O$ 3 times.

Dry under nitrogen and store at −20° C.

The resulting spectrophotometric scan shows that the PCB presents two peaks of absorption, at 370 and 690 nm.

Antioxidant Superiority of the Klamath Algae's Phycocyanins in Comparison with other Phycocyanins.

Phycocyanins (PC) are the blue pigments typical of all blue-green microalgae, but with different structural and functional characteristics in each specific microalga (22). As to sources of PC used as nutritional supplements and potential natural drugs, research has so far focused on *Spirulina*. *Spirulina*'s phycocyanins have shown to possess antioxidant (23) and antinflammatory (24,25,26) properties, with significant activity on different physiological areas such as liver (27), respiratory system (28), and brain (29,30). Given the lack of research on other phycocyanins such as those of Klamath algae, we have comparatively measured the antioxidant capacity of the aqueous extract from AFA (Klamath) algae in relation to the product Serum Bleu™, a liquid extract concentrating PC from microalga *Spirulina platensis*.

Figure 8:
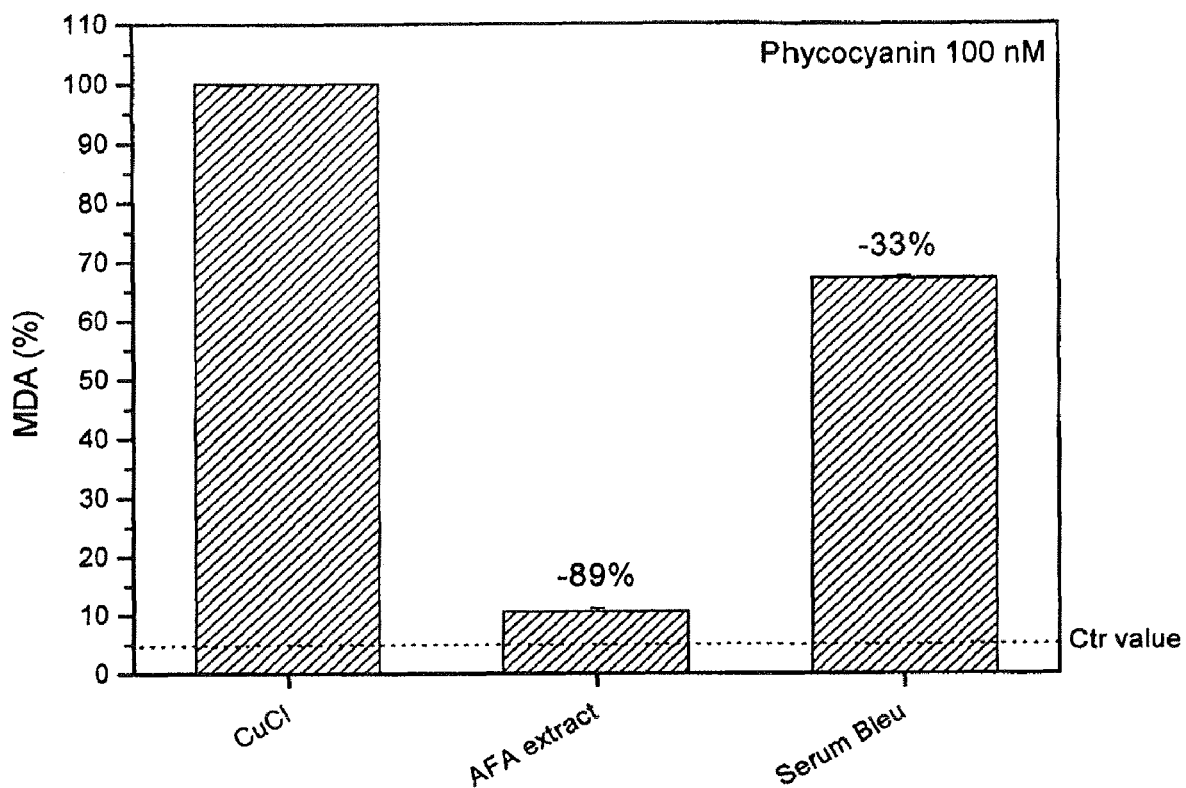
FIG. 8 shows the reduction in malondialdehyde (MDA) levels in plasma samples oxidized by $CuCl_2$ and pre-incubated with an AFA Klamath extract and the SERUM BLUE™ extract.

The reduction of MDA (malondialdehyde) levels in plasma samples oxidized by $CuCl_2$ and pre-incubated with the two extracts is shown in FIG. 8, where it is possible to see that the extract at a PC concentration of 100 nM is by far more efficient in inhibiting the oxidation of plasma lipids, with the inhibition of the MDA formation reaching the level of 89% vs. an inhibition of 33% produced by Serum Bleu™ at the identical PC concentration of 100 nM. This shows that at the same PC concentration the AFA extract is significantly more powerful than the *Spirulina*'s extract. Such difference can be attributed to two distinct and complementary factors: a) a structural and thus functional diversity of the two types of PC; b) the presence in the extract of further antioxidant factors that are missing, as in the case of the phytochrome, or more scarcely present, such as MAAs, in other microalgae such as *Spirulina*. The higher antioxidant power of AFA PC in relation to C-PC (from *Spirulina*) is however shown also through a comparison with the data available in the literature on lipoperoxidation.

Plasma and Erythrocytes Lipid-Peroxidation

When tested for its anti lipid-peroxidation properties on rat liver microsomes oxidized with AAPH, C-PC from *Spirulina* inhibited the production of TBARS (conjugated diens, MDA) with an IC50 of 11.35 µM (23, Bhat et al.). C-PC from *Spirulina* has also been tested by Romay & Gonzales (41) against human erythrocytes lysis induced by AAPH: the IC50 in this case was 35 µM.

We tested the same ability of both AFA-PC and its PCB to inhibit the formation of MDA on: a) human plasma oxidized by $CuCl_2$; b) on RBC (red blood cells or erythrocytes) oxidized by AAPH. We also tested the ability of AFA-PC and PCB to inhibit the AAPH-induced lysis of erythrocytes. In the former case, plasma samples were obtained after centrifugation of the heparinized blood from healthy volunteers at 1500 g for 10 min. The extent of lipid oxidation in plasma samples incubated for 2 h at 37° C. with PBS (control) or with 100 µM $CuCl_2$ in the presence of increasing concentrations of PC or PCB (range 0.1-1 µM) was assayed by measuring TBA-reactive substances at 535 nm (42). In relation to erythrocytes, heparinized blood samples were obtained from healthy volunteers via venapuncture after obtaining informed consent. Red blood cells (RBC) were isolated by centrifugation at 1500 g for 10 min, washed three times with PBS and finally re-suspended using the same buffer to an hematocrit level of 5%. RBC were incubated with PBS (control) or 50 mM AAPH for 4 hours at 37° C. in the presence of different concentrations of PC or PCB (range 0.1-1 µM). TBA-reactive substances, mainly malonyldialdehyde (MDA), as indicators of lipid peroxidation, were assayed as previously described (42). Briefly, a 1 ml reaction mixture was incubated at 95° C. for 1 h with 250 µl of TBA (0.67%) and 100 µl of $H_3PO_4$ (0.44 M); then 150 µl of TCA (20%) were added. After centrifugation, the peroxide content in the supernatant was determined using the molar extinction coefficient ($OD_{535}$) of MDA.

Figure 9A:
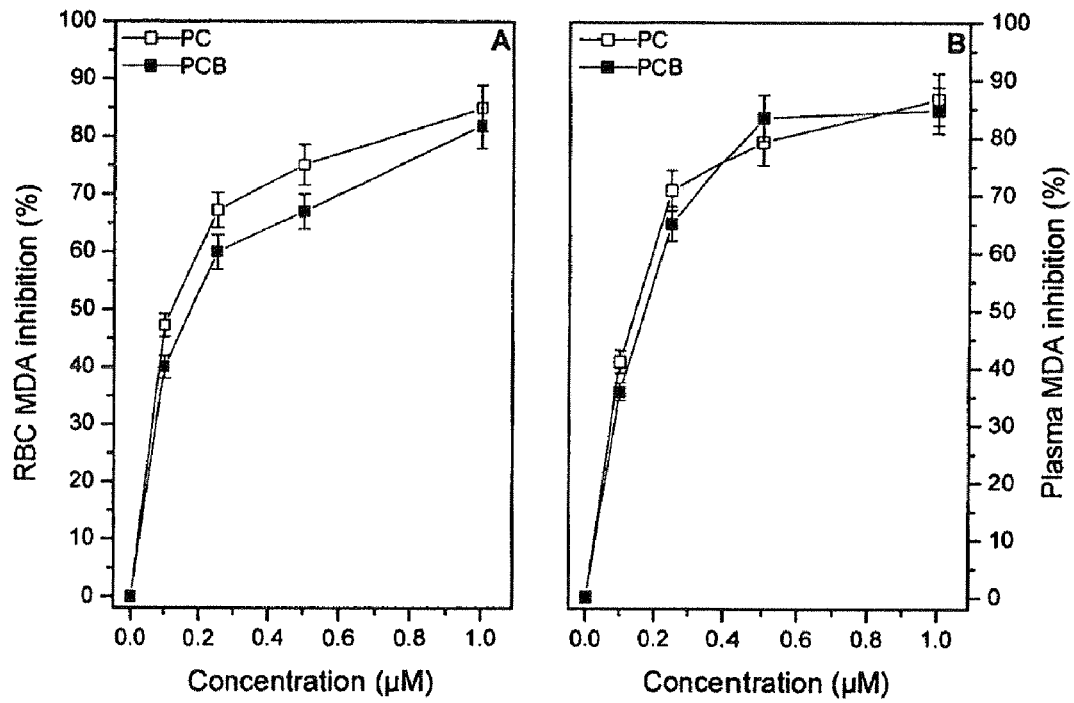
FIG. 9A shows that AFA-PC and its chromophore, PCB, inhibited the lipid peroxidation in erythrocytes in a dose-dependent manner.

As reported in FIG. 9A, PC and PCB inhibited in a dose-dependent manner (p<0.05 for each concentration tested) the extent of lipid peroxidation in RBC (erythrocytes) incubated for 2 hours at 37° C. with the peroxyl radical generator AAPH (panel A); at the same time, PC and PCB dose-dependently protected plasma lipids from metal-induced oxidation (p<0.05) in samples incubated for 2 hours at 37° C. with $CuCl_2$ (panel B). In both inhibition experiments, $IC_{50}$ values were approximately 0.140 µM and 0.160 µM for PC and PCB (vs. 11.35 µM of C-PC from *Spirulina*).

Figure 9B:
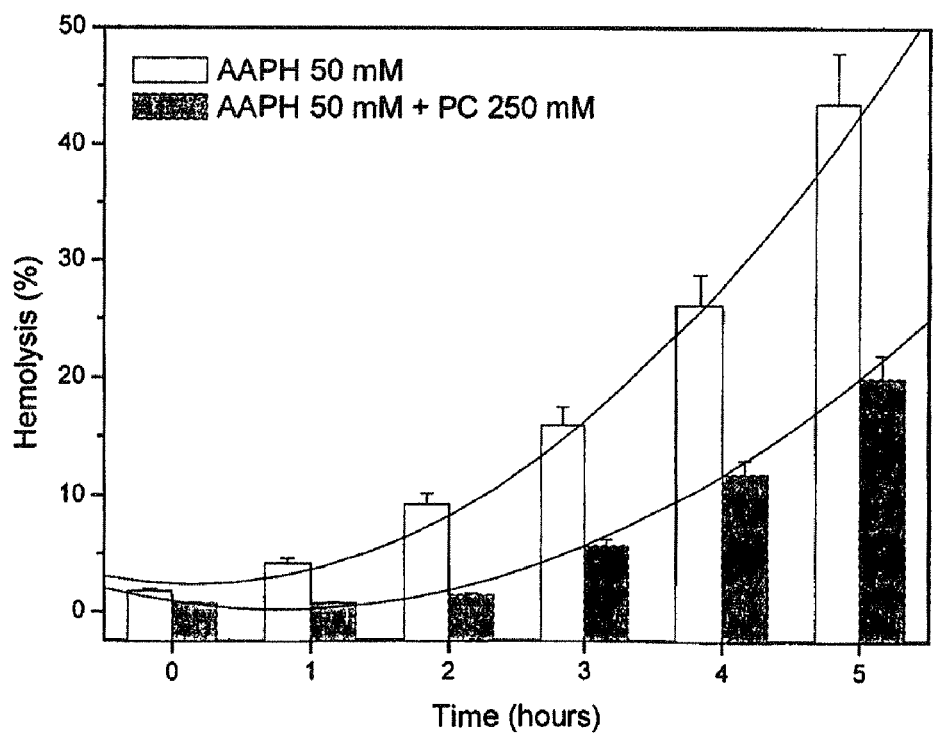
FIG. 9B shows that AFA-PC inhibits the AAPH-induced lysis of erythrocytes.

We also tested the ability of AFA-PC to inhibit the AAPH-induced lysis of erythrocytes: as shown by FIG. 9B, AFA-PC has been able to constantly (that is from the 1st to the 6th hour) inhibit the lysis of erythrocytes more than 50% with just 250 nM of AFA-PC (vs. the IC50 of 37 µM for C-PC from *Spirulina*).

Even taking in account some difference in the testing method or concentration, in both cases the superiority of AFA-PC over C-PC from *Spirulina* is truly remarkable, the difference in IC50 values being 75 to 150 times in favour of AFA-PC. An even greater indication of the difference in potency can be seen by the fact that, as reported in the same study by Bhat et al. (23) lipid-peroxidation is inhibited 95% with a *Spirulina* C-PC dosage of 200 µM. In FIG. 9A we can see that, to obtain a similar degree of inhibition only 1 µM of AFA-PC is required, that is 200 times less. This confirms that the significant difference between the C-PC on its own and the C-PC/PEC complex which characterizes AFA algae and its extracts is due precisely to PEC, the only element that differs, thus showing PEC to be a very powerful molecule on its own.

In addition, the IC50 of PC is slightly lower than that of PCB. This is somewhat surprising, given that the PCB, being considered its most active principle, once purified and thus more concentrated, should be significantly stronger than the whole molecule of which is the active component. The fact that it is actually slightly weaker, though still very powerful, means that in the whole PC there are other factors that may actually be even more potent than the PCB itself. We know that the whole PC contains PEC, besides C-PC and its PCB chromophore, which includes as its chromophores both PCB and PVB (phycoviolobilin). Therefore, we believe that the factor creating a significant difference in potency between the purified PCB and the whole PC is precisely the PEC component, particularly its PVB chromophore, which is considered a very strong antioxidant.

Evaluation of the Antioxidant Capacity (ORAC) of AFA-PC and its PCB

The ORAC (Oxygen Radical Absorbance Capacity) method is widely used to determine the total antioxidant capacity of pure and composed substances, measuring their activity in comparison to the Trolox (an hydrosoluble analog of vitamin E) as a reference molecule (31). However, up to now it has never been used to determine the antioxidant capacity of pure natural molecules from cyanobacteria such as PC and PCB.

The ORAC assay was carried out at 37° C. on a FLUOstar OPTIMA spectrofluorimeter (BGM LABTECH, Germany) at 485 nm excitation and 520 nm emission, using the method of Ou et al. (32) with minor modifications. Briefly, in the final assay mixture, fluorescein (FL) (0.05 µM) was used as a target of free radical attack, with AAPH (4 mM) as a peroxyl radical generator. Trolox (1 µM) was used as a control standard and phosphate buffer as a blank. The concentrations of tested compounds in the assay mixture ranged from 0.025 µM to 2 µM. All substances were dissolved and diluted with 75 mM Na-phosphate buffer pH 7; PCB solution was made by dissolving the compound first in ethanol and then bringing the solution to the desired concentration with the buffer. All samples were run in triplicate. Fluorescence was recorded every 5 min after AAPH was added. Final results (ORAC values) were calculated using the differences in the areas under the fluorescence decay curves (AUC) between the sample and blank and expressed as Trolox equivalents:

$$\text{ORAC value} = [(\text{AUC}_{sample} - \text{AUC}_{blank})/(\text{AUC}_{trolox} - \text{AUC}_{blank})] \times (\text{molarity}_{trolox}/\text{molarity}_{sample})$$

Linear regression analyses of ORAC values (y) versus AA, GSH, PC and PCB concentrations (x) adequately described the data as assessed by the correlation coefficient.

Figure 10:
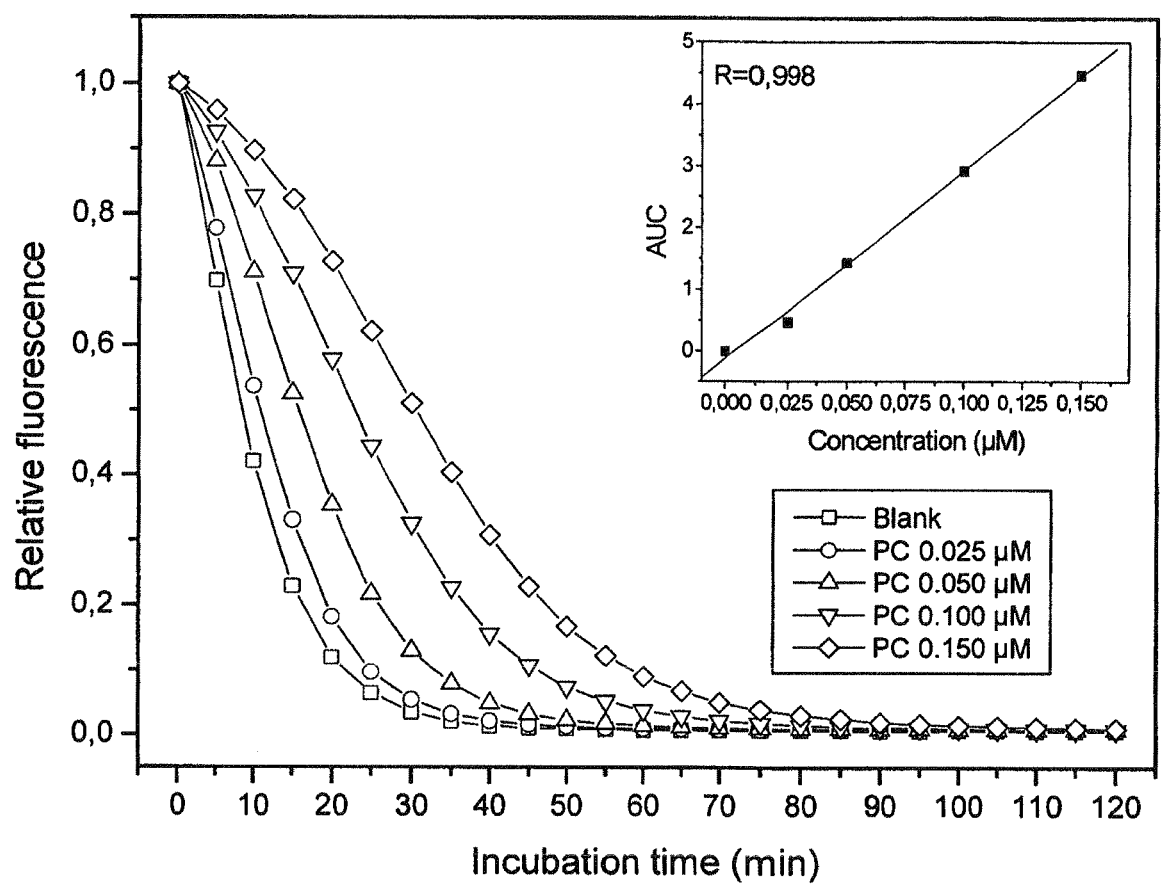
FIG. 10 shows the effects of AFA-PC on the kinetics of the loss of fluorescein's fluorescence after the addition of AAPH.

PC is a fluorescent water-soluble protein that upon excitation at 620 nm, emits at 647 nm this own fluorescence did not interfere with FL emission at 520 nm and no modifications of fluorescence intensity were evidenced after PC was added to the reaction mixture. The effects of PC on the kinetics of FL fluorescence loss after addition of AAPH are reported in FIG. 10, clearly showing a linear correlation between PC concentrations (ranging from 0.025 to 0.150 µM) and the net area under the fluorescence decay curve (AUC) ($r=0.998$, $p<0.0001$).

Figure 11:
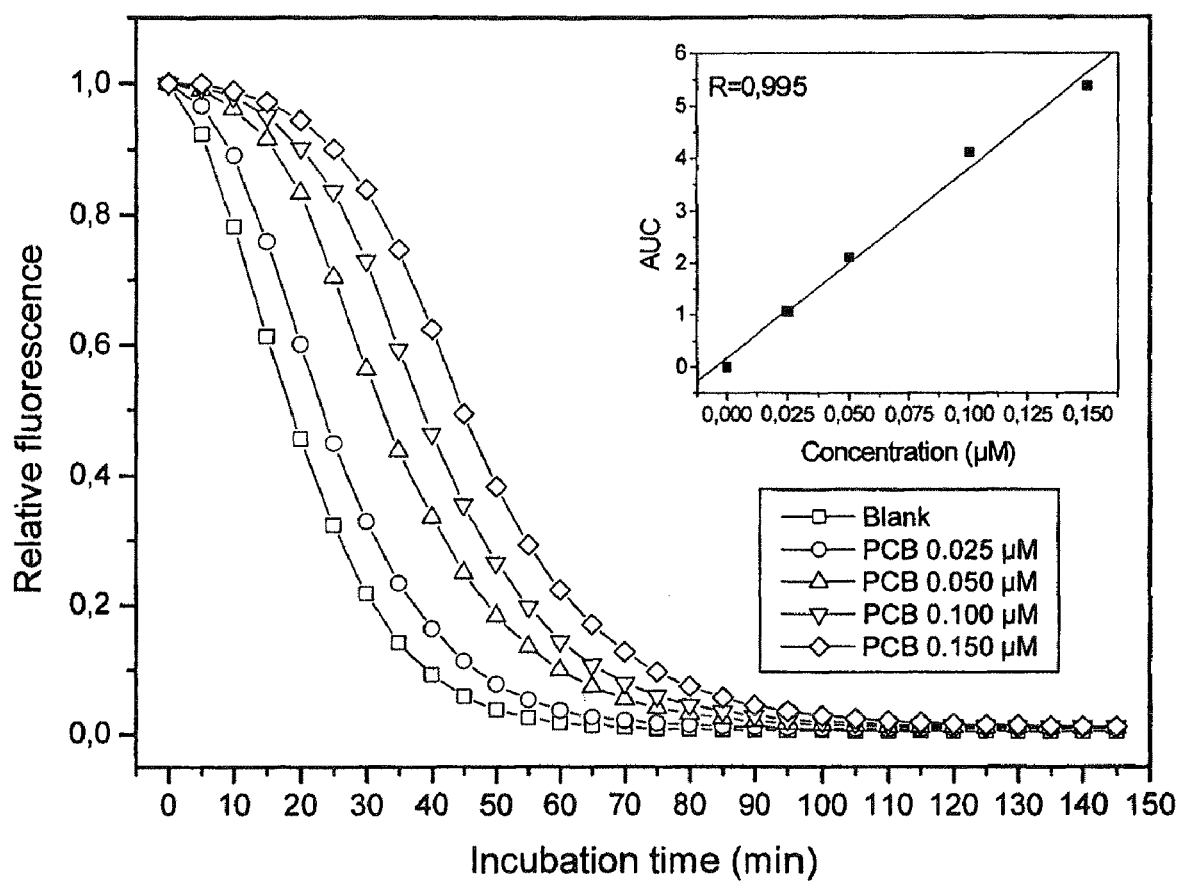
FIG. 11 shows the kinetics of quenching of fluorescein's fluorescence at different concentrations of PCB.

The chromophore PCB is responsible for the brilliant blue color of PC and after release from the protein, presents two characteristic peaks of absorption at 370 and 690 nm that, as in the case of PC, did not affect FL fluorescence. FIG. 11 shows the kinetics of FL quenching with different bilin concentrations and the positive correlation ($r=0.995$, $p<0.0005$) of AUC versus PCB concentrations (range 0.025-0.150 µM).

Figure 12:
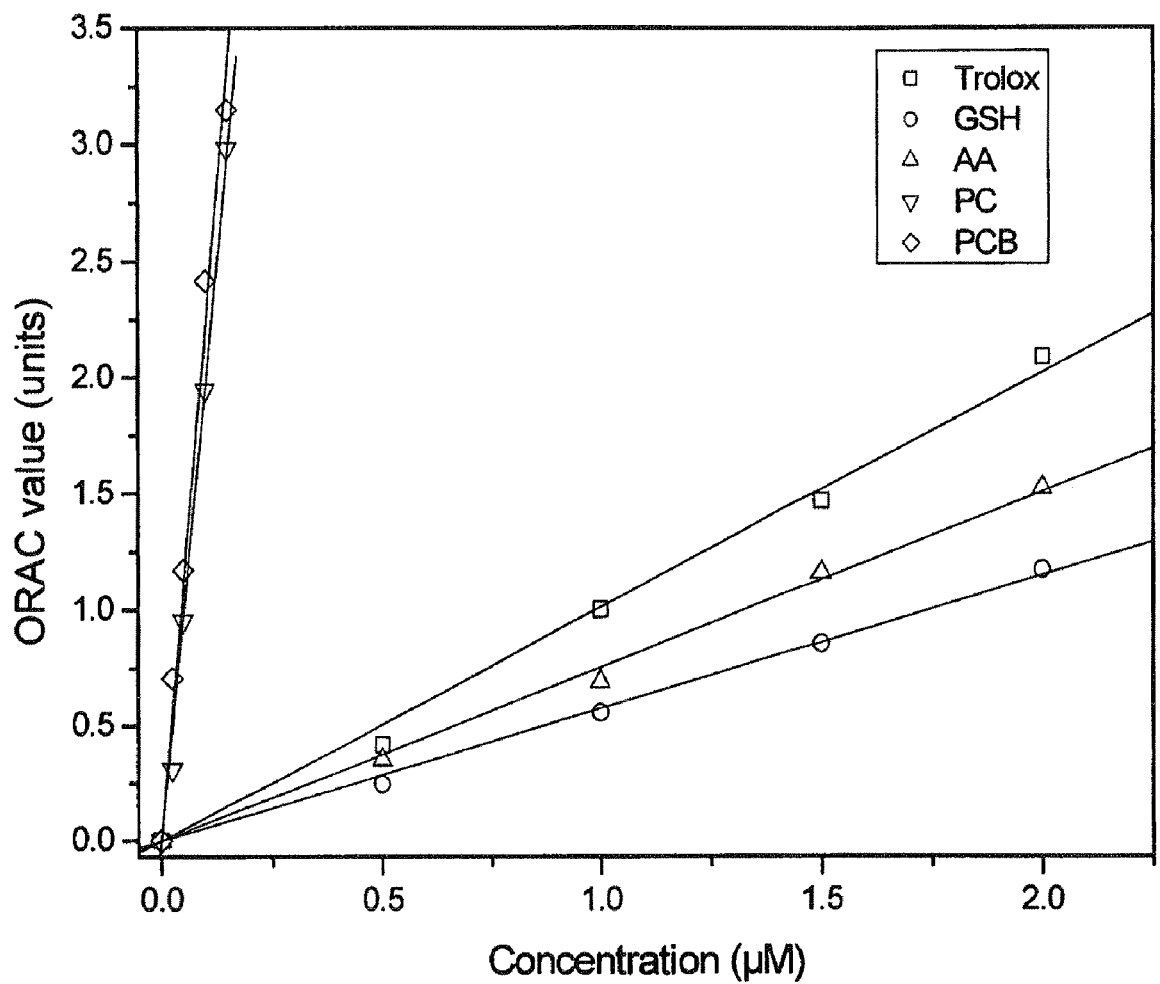
FIG. 12 shows the linear regression analysis of Trolox, GSH, AA, PC and PCB with respect to their ORAC value.

Finally, the ability of pure PC and PCB to directly quench peroxyl radicals has been compared to those of well-known pure antioxidants molecules. FIG. 12 reports the linear regression analysis of Trolox, GSH, AA, PC and PCB with respect to their ORAC value. Based on these data, we found that PC and PCB had the highest ORAC values (20.33 and 22.18 Trolox equiv., respectively), whereas GSH and AA showed the lowest (0.57 and 0.75). The fact that also in the ORAC test the value of AFA-PC and PCB are quite similar confirms the very important role played by PEC in the AFA-PC.

No references on ORAC values are available for the natural compounds cited; however, to our knowledge, the ORAC value of PCB (whether expressed as µmol Trolox/µmol PCB or as µmol Trolox/mg PCB) is the highest found in literature as regards pure antioxidant molecules for which the ORAC activity has been evaluated using FL as fluorescent probe ($\text{ORAC}_{FL}$). As example, Ou et al. (Ou et al., 2001) determined the antioxidant capacity of different phenolic compounds by the $\text{ORAC}_{FL}$ method, and the highest values found were 7.28 and 6.76 µmol Trolox/µmol compound which, if the relative ORAC values are expressed as µmol Trolox/mg sample rather than µmol Trolox/µmol sample, becomes 24.0 and 23.3 µmol Trolox/mg compound, for flavonoids quercetin and (+)-catechin, respectively; while the ORAC for the PCB becomes 37.0 µmol Trolox/mg.

Protective Effect of AFA-Phycocyanin and its PCB on Cultured Cells.

Figure 13:
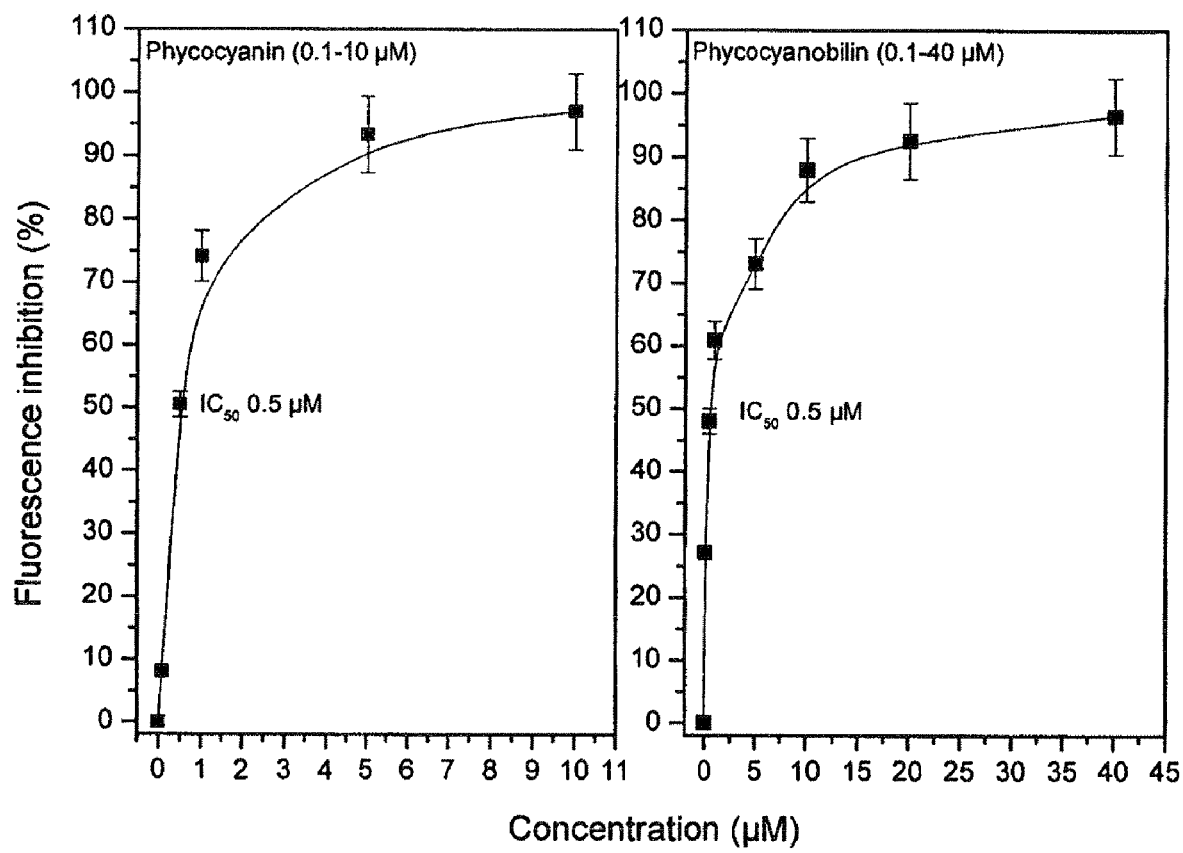
FIG. 13 shows a dose-dependent inhibition of intracellular fluorescence in Jurkat cells upon simultaneous addition of $H_2O_2$ and phycocyanin (left panel) and $H_2O_2$ and phycocyanobilin (right panel).

Starting from the Basic extract, and following the methodology already described, we have purified the AFA-phycocyanin, with its C-PC/PEC complex, to test its antioxidant properties on live cultured cells. The Jurkat cells (immortalized line of leucemia T-lymphocytes) have been subjected to oxidative stress with 500 µM H2O2, together or without increasing dosages of AFA-PC and PCB. The fluorescence emitted by the intracellular probe (dichlorofluorescein), following oxydation from H2O2, has been recorded after 30 minutes of incubation with H2O2 through a fluorimeter (exc. at 492 nm and emission at 520 nm). By incubating cells with both AFA-PC (range 0.1-10 µM) and 500 µM H2O2 for 30 minutes we observe a dose-dependent protective effect with a reduction of intracellular fluorescence induced by H2O2, with an $IC_{50}$ of 0.5 µM, and a 100% inhibition (non-oxidized cells) at 10 µM (FIG. 13).

The antioxidant properties of the whole PC, composed of C-PC and PEC, resides in its chromophores, which are phycocyanibilin (PCB) for C-PC and both PCB and PVB (phycoviolobilin) for PEC. We have purified the C-PC chromophore PCB, to test it on cultured cells oxidized with H2O2 (range FCB 0.1-40 µM). Also in this case we observe a dose-dependent antioxidant effect with an $IC_{50}$ of 0.5 µM, and a 100% inhibition (non-oxidized cells) at 40 µM (FIG. 13).

At the concentrations that have been tested, both AFA-PC and the PCB incubated for 30 minutes with the cultured cells and without H2O2 do not have any oxidative effect, as shown by the fact that there is no increase of intracellular fluorescence.

Most importantly, to evaluate the cellular absorption of PC and PCB, both compounds have been pre-incubated for 2 hrs. with the cells; afterwards, the medium has been washed, to exclude any unabsorbed PC and PCB, and the cells have been oxidized for 30 min. with H2O2. As shown by the FIG. 14, there is a dose-dependent inhibition of intracellular fluorescence. This means that the cell is able to retain both antioxidant molecules, either in the membrane or in the cytoplasm.

This is a very important finding, as it proves that the antioxidant activity of the two molecules are very likely effective in vivo for therapeutic purposes.

Whereas studies done on the purified *Spirulina* C-PC had already proven its ability to penetrate cellular cytosol (43), this is the first demonstration of the ability of the purified PCB to enter and being retained in the cell. Furthermore, this is the first time that the same ability is demonstrated for the specific AFA-PC (C-PC/PEC complex). At the concentrations tested, both PC and PCB incubated for 2 hrs. with the cells did not produce any oxidative effect, as shown by the fact that there is no increase in the intracellular fluorescence.

Figure 14:
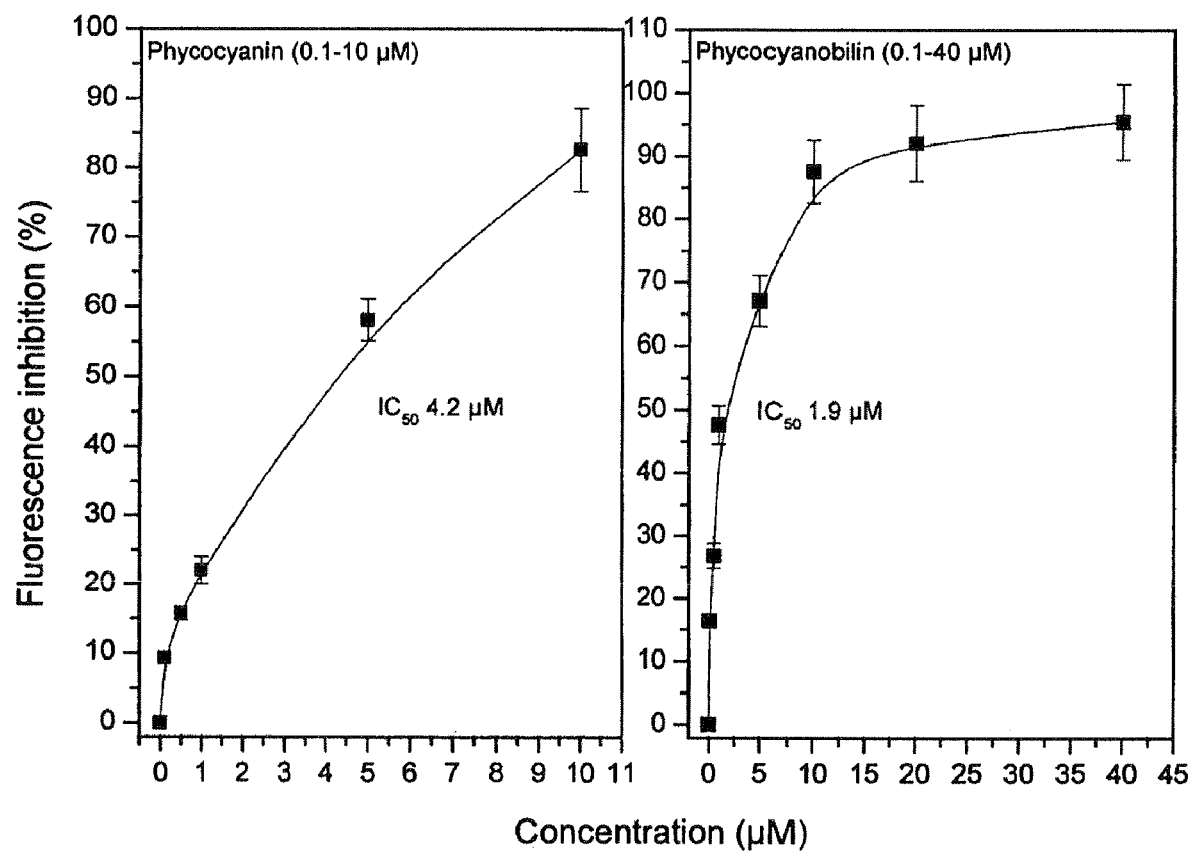
FIG. 14 shows a dose-dependent inhibition of intracellular fluorescence in Jurkat cells pre-incubated with phycocyanin (left panel) and phycocyanobilin (right panel) and then exposed to oxidative stress by the addition of $H_2O_2$.

Whereas in FIG. 13, where oxidative agent and antioxidants were added at the same time, we see that the degree of cell protection afforded by PC and PCB is equivalent; in the absorption test, as shown from FIG. 14, PCB's antioxidant effect results to be slightly faster (IC50 1.9 µM for PCB vs. 4.2 µM for PC); and also slightly higher (more than 90% protection by PCB; less than 90% by PC). This means that the degree of absorption of the PCB, relative to the PC, is indeed slightly higher (as could be expected, given the more purified nature of the PCB). Nevertheless, the degree of absorption is truly remarkable for both compounds, given that in both cases is very close to the degree of protection afforded with the simultaneous addition of antioxidants and oxidative agent.

On the other hand, this live cells test confirms a previous consideration on the essential relevance of the PEC component for the antioxidant property of the whole PC. As shown by both FIGS. 13 and 14, the fact that the whole purified PC has the same very high antioxidant potency as the purified PCB, the concentration of which is much higher after purification relative to its concentration as part of the whole PC, indicates that the PCB is not the only active agent of PC, and that in fact whatever other agent or agents (starting with PVB) are present in PC, they are very likely significantly more potent than PCB itself.

Novel Determination of Synergic Factors that Make the Extract More Effective than the AFA-Phycocyanins Contained in it.

We have seen that the AFA-PC, with its C-PC/PEC complex, is significantly more potent than the pure C-PC from other algae such as *Spirulina*, But there are in Klamath algae other factors which explain also the superiority of its extracts, starting with the Basic extract, relative to its main antioxidant and antinflammatory principle, the phycocyanins/phycoerithrocyanin complex.

The main factor that explains such difference is the second element that composes the wider phycobiliprotein complex constituting the light control system of AFA algae, namely its specific phytochrome, in absolute terms the most powerful antioxidant principle so far found in the algae. Further factors can be identified in the specific molecules typical of all algae called "mycosporine-like aminoacids" or MAAs, of which Klamath algae is particularly rich; and a series of nutritional molecules whose antioxidant and antinflammatory action is already known, such as chlorophyll, beta-carotene and carotenoids, plus various vitamins and minerals.

A) Identification of "AFA-Phytochrome", a Unique Phytochrome Typical of Klamath Algae Phytochromes are photoreceptors, pigments that plants use to detect light, and that are sensitive to light in the red and far-red region of the visible spectrum. They perform many different functions in plants, including the regulation of flowering (through circadian rhythms), germination and the synthesis of chlorophyll. The latter is particularly relevant in relation to AFA algae, because the presence of this unique type of phytochrome in AFA may be explained by its lack of the other phycobiliprotein commonly used by other cyanobacteria to complement C-phycocyanin in the process of photosynthesis, namely allo-phycocyanin. While, as we have seen, the place of allo-phycocyanin in Klamath algae is taken by PEC, it is likely that PEC alone is not sufficient, especially considering that Klamath alga lives in a non-tropical environment which needs a high light harvesting efficiency, and so AFA algae seems to integrate its higher needs with its own phytochrome.

While AFA phytochrome, which has been detected and is described here for the first time, has its own peculiar structure, it is still possible to define it as a representative of the general family of phytochromes. Over the years, different types of phytochromes have been found in plants, which not only have different phytochrome genes (3 in rice, but 6 in maize, for instance), but most of all the specific phytochrome of each plant, or at least of each plant family, has significantly different protein components and thus structure. Nevertheless, what makes them all phycochromes is that they all use the same biliprotein, called phytochromobilin, as a light-absorbing chromophore, This chromophore is similar to the phycocyanin's chromophore phycocyanobilin, and is characterized by being a single bilin molecule consisting of an open chain of four pyrrole rings (tetrapyrroles). Since the active principle of all phytochromes, in their different general structure, still remains this chromophore, even taking in account some variations among different species, it is possible to attribute the properties of each single phytochrome to other phytochromes. (44) More specifically, in its $P_r$ normal state this biliprotein absorbs light at a maximum of 650-670 nM; whereas when activated by red light it is transformed into $P_{fr}$ with an absorbance maximum of 730 nM.

AFA Phytochrome Description and Purification

AFA-phytochrome, while having a relatively unique structure, has a biliprotein as its chromophore that absorbs light in the red/far-red spectrum. To establish its structure and activities we have purified the phytochrome with the following protocol:

Suspend 1 g of extract in 10 ml of 1 K-phosphate buffer, pH 7.0.

Vortex twice for 1 min with half their volume.

Incubate cells for 35' with 2% Triton X 100.

Centrifuge at 28000 rpm for 16-18 h.

Collect supernatant on a sucrose density step gradient.

Spin the gradient using swing-out rotors at 150000 g for 12 h.

Store at −20° C.

Figure 15:
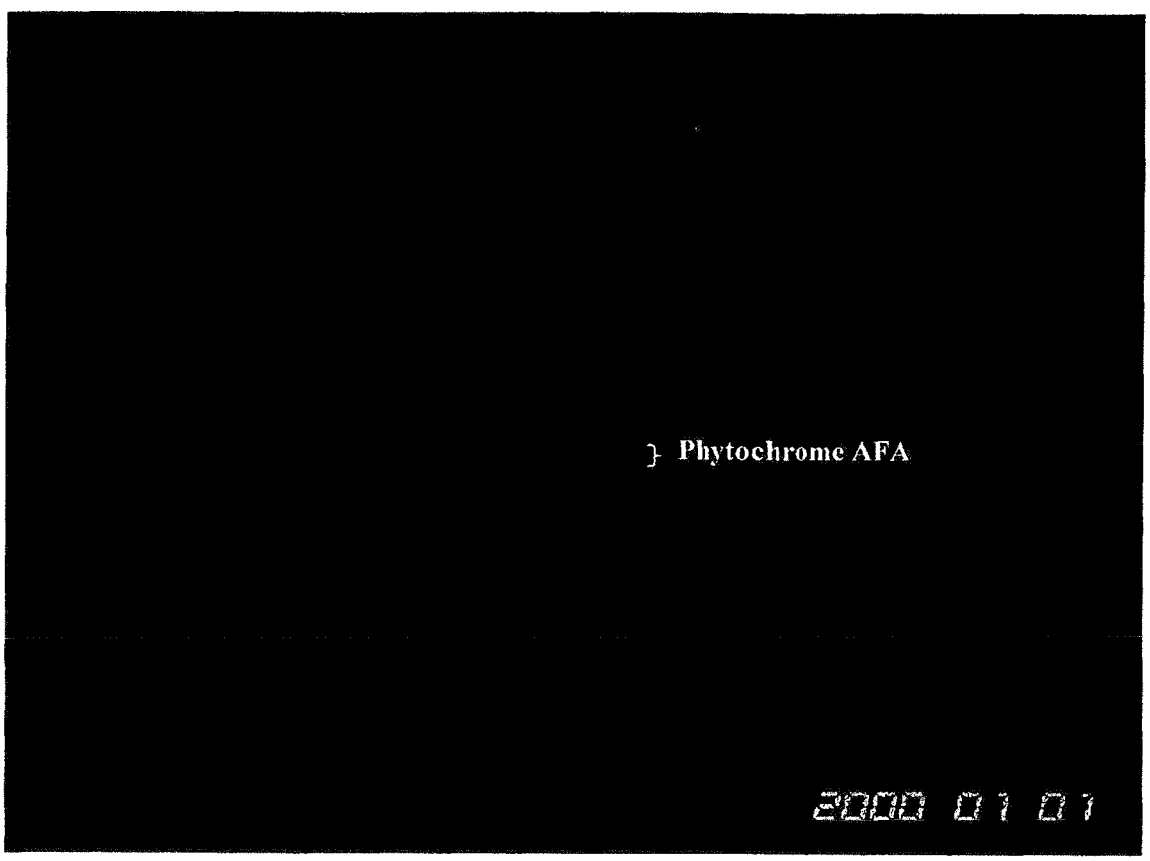
FIG. 15 shows the approximate molecular weight of AFA-phytochrome.

The phytochrome corresponds to the lysate band of an intense orange color, which is visible at approximately 1M of sucrose, while the phycobilisome stands at approximately 0.75M. This relation of the two bands also gives a reliable indication about the molecular weight of the phytochrome present in the algae, which is about 4 times that of the trimeric AFA-PC: the latter being 121Kd, we can preliminarily establish the MW of AFA-phytochrome at approximately 480Kd (FIG. 15)

Figure 16:
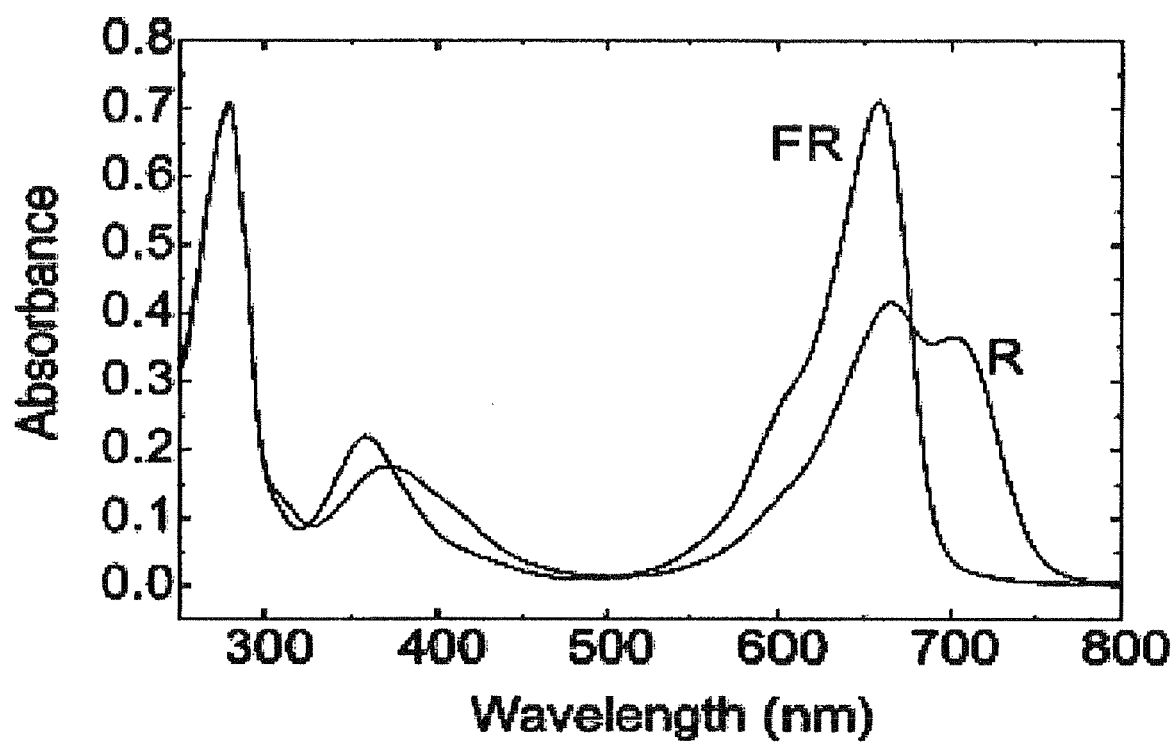
FIG. 16 shows the light-absorbing properties of AFA-phytochrome.

Tested for its light-absorbing properties, the phytochrome shows to absorb light with two peaks at 672 nM and 694 nM, which corresponds respectively to $P_r$ (red-light absorbing) e $P_{fr}$ (far-red light absorbing) forms in a state of balance (FIG. 16).

As to the quantity of phytochrome contained in AFA, our first evaluation gives the following preliminary result: 2 mg./gr. (or 0.2% DW). As to the extracts, the concentration increases to approximately 0.5% in the Basic Extract, and approx. 1% in the Extract B.

Antioxidant Activity

Figure 17:
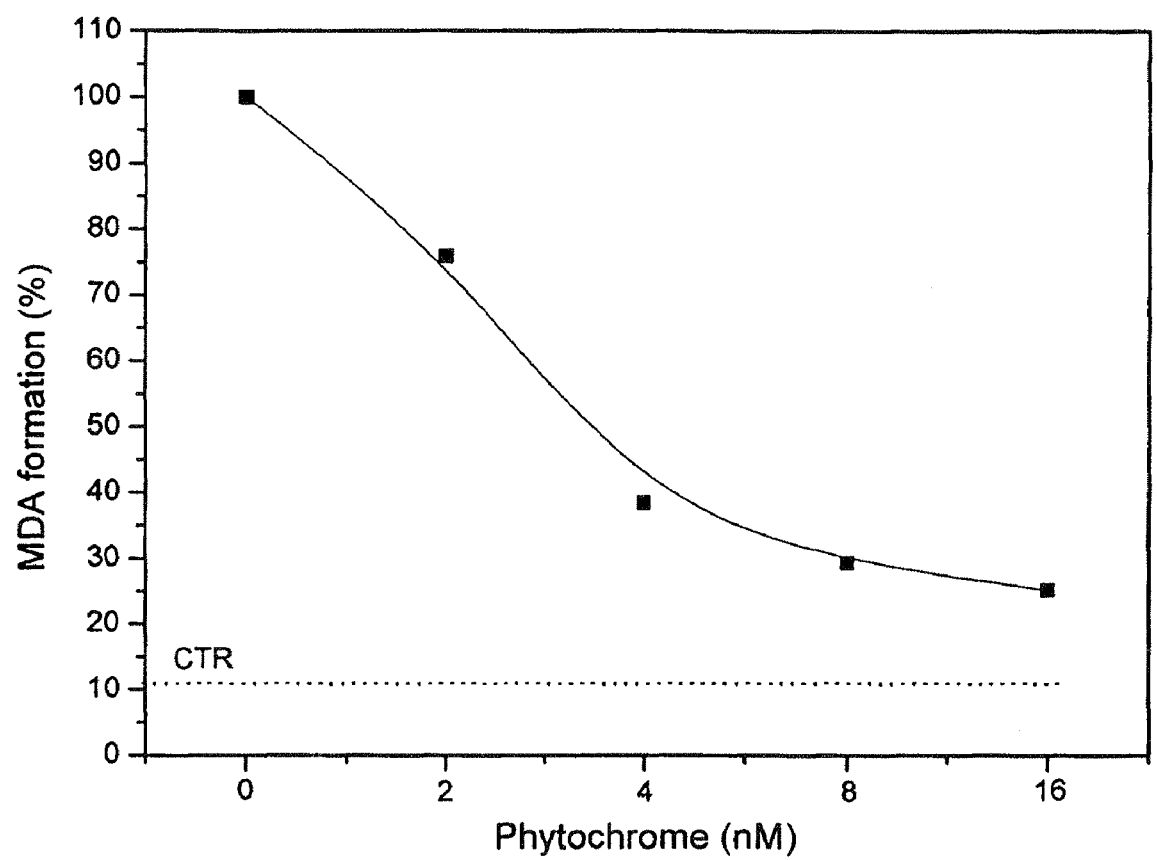
FIG. 17 shows the reduction in MDA levels in plasma samples simultaneously incubated with $CuCl_2$ and increasing quantities of AFA-phytochrome.

The purified AFA-phytochrome has shown to be a very powerful antioxidant. The incubation for 2 hrs. of human plasma samples with oxidative agent $CuCl_2$ at 100 μM generates increased levels of malondialdehyde (MDA), a late byproduct of lipid peroxidation which is measured through spectrophotometer at 535 nm after a reaction with thiobarbituric acid (TBA test). When plasma is incubated for 2 hrs at 37° C. with $CuCl_2$ 100 μM together with increasing quantities of AFA-phytochrome (2-16 nM) extracted from AFA algae, it is possible to observe a very strong dose-dependent reduction of the MDA levels (FIG. 17). In fact, we obtain an almost complete inhibition of lipoperoxidation, with MDA levels close to control, with just 16 nM of AFA phytochrome. It is remarked that the IC50 of 3.6 nM is 45 times less than the IC50 obtained for the PCB. There is no doubt that the phytochrome herein described is responsible for the higher antioxidant activity observed with the Basic Extract compared to the AFA-PC.

B) Identification of "Mycosporine-Like Aminoacids" (MAAs) of Klamath Algae

MAAs are water soluble compounds, characterized by a cyclohexenone or cyclohexenimine chromophore conjugated with a nitrogen atom substituting for an amino acid or its amino alcohol (as shown in FIG. 4).

They have an absorption maximum ranging from 310 to 360 nm and an average molecular weight of around 300 (4). MAAs are passive sunscreens, preferentially absorbing UV photons followed by a dissipation of the absorbed radiation energy in the form of harmless heat without generating photochemical reactions and thereby protecting, at least partially, photosynthesis and growth of phototropic organisms. Besides having a role in UV screening, it has been demonstrated that several MAAs also show antioxidant properties acting as scavengers of photodynamically generated reactive oxygen species in organisms (5).

We tested the presence of MAAs in the cyanophyta *Aphanizomenon flos-aquae* and its extract. Whereas most of the cyanobacteria reported to date contain shinorine as their primary MAAs; we found a rare occurrence of porphyra-334 as the primary MAA in *Aphanizomenon flos-aquae* in addition to a small amount of shinorine.

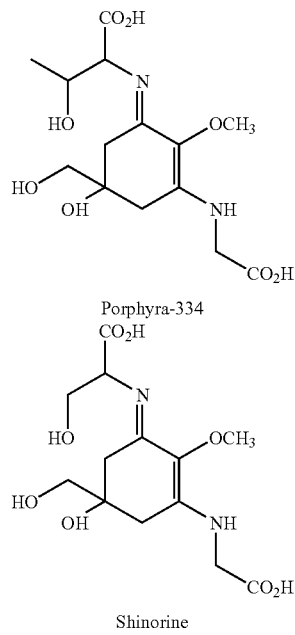

Porphyra-334

Shinorine

Extraction, Purification and Quantification of MAAs

MAAs were extracted as previously reported (6). Briefly, 20 mg of AFA powder or 20 mg of extract were extracted in 2 ml of 20% (v/v) aqueous methanol (HPLC grade) by incubating in a water bath at 45° C. for 2.5 h. After centrifugation (5000 g; GS-15R Centrifuge, Beckman, Palo Alto, USA), the supernatant was evaporated to dryness and re-dissolved in 2 ml 100% methanol, vortexed for 2-3 min and centrifuged at 10000 g for 10 min. The supernatant was evaporated and the extract re-dissolved in the same volume of 0.2% acetic acid for the analysis in HPLC or in 200 μl of phosphate buffer (PBS) for the evaluation of antioxidant properties. The samples were filtered through 0.2 μm pore-sized syringe filters (VWR International, Milan, Italy) before being subjected to HPLC analysis, or to the test of antioxidant properties (see below).

The MAAs of AFA and of its extracts, have an absorption maximum of 334 nm. Further purification of MAAs was done using a HPLC system (Jasco Corporation, Tokyo, Japan) equipped with a Alltima C18 column and guard (4.6×250 mm i.d., 5 μm packing, Alltech, Milan, Italy), according to the literature (7). The wavelength for detection was 330 nm; the mobile phase was 0.2% acetic acid at a flow-rate of 1.0 ml min$^{-1}$. Identification of MAAs was done by comparing the absorption spectra and retentions time with standards such as *Porphyra* and *Pterocladia* sp., mainly containing porphyra-334, shinorine and palythine, kindly provided by Dr Manfred Klisch, Friedrich-Alexander-Universitat, Erlangen, Germany. Absorption spectra of samples were measured from 200 to 800 nm in a single-beam spectrophotometer (DU 640, Beckman, Palo Alto, USA). The raw spectra were transferred to a computer and treated mathematically for the peak analyses of MAAs.

Figure 5:
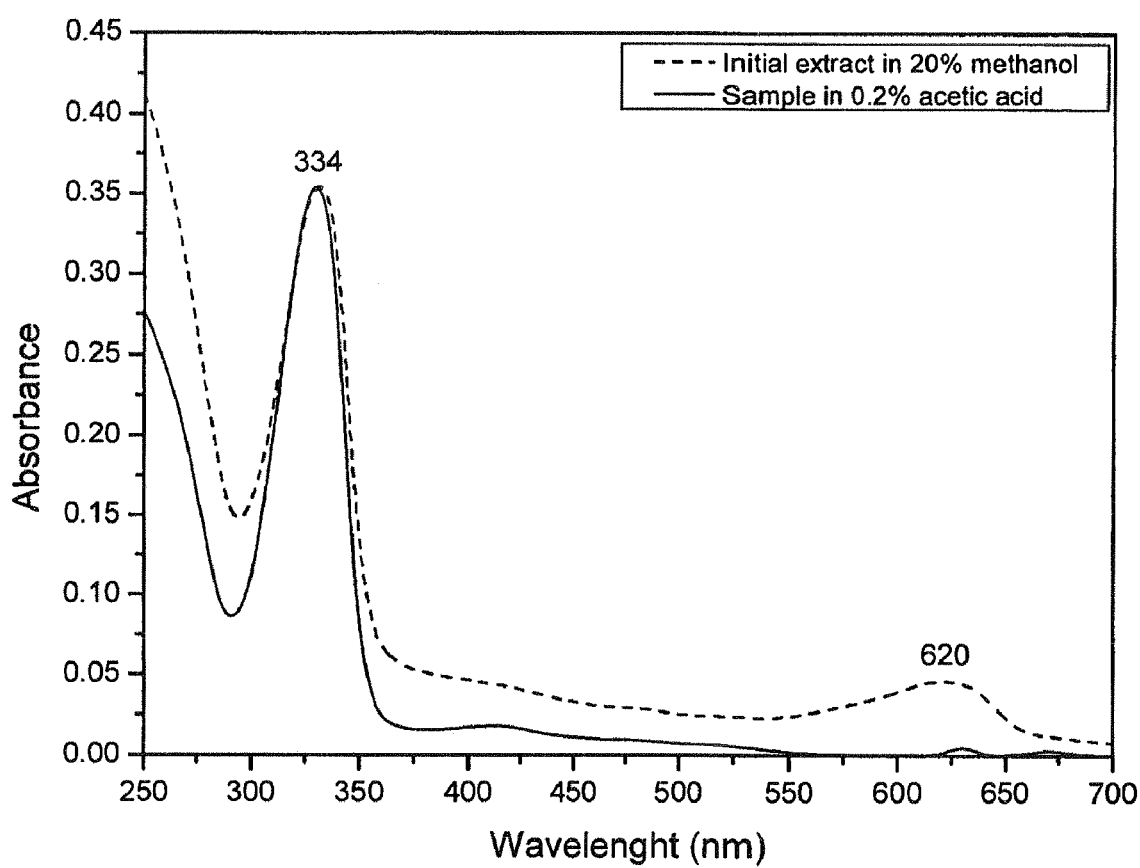
FIG. 5 shows a spectrophotometric scan of partially purified MAAs.

MAAs were partially purified from AFA sample and from the extract as described earlier. Extraction of samples with 20% methanol at 45° C. for 2.5 h resulted in a prominent peak at 334 nm (MAAs); even if small amounts of photosynthetic pigments (such as phycocyanin at 620 nm) were also extracted with this procedure (see the following figure, dashed line). MAA samples were further treated with 100% methanol in order to remove proteins and salts and finally with 0.2% acetic acid to remove non polar-photosynthetic pigments. The resultant partially purified MAAs had an absorption maximum at 334 nm (FIG. 5, solid line).

Figure 6:
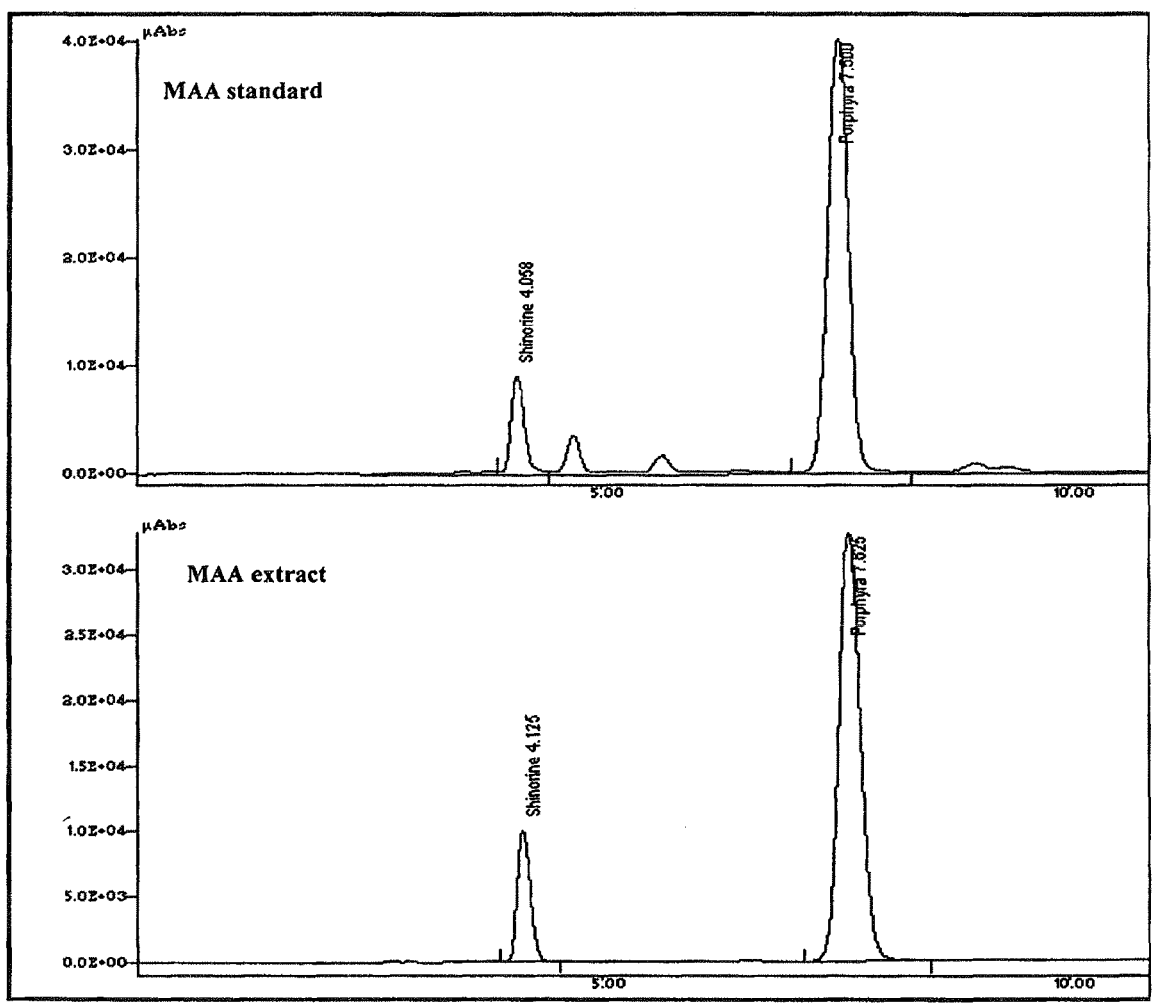
FIG. 6 shows a chromatogram of MAAs purified by HPLC.

Further analysis and purification of MAAs was done by HPLC with a view to find whether the compounds absorbing at 334 nm was a single MAA or a mixture of more than one MAAs. The chromatogram of the sample (FIG. 6) shows the presence of two MAAs with retention times of 4.2 (peak 1) and 7.6 min (peak 2) that were identified as shinorine and porphyra-334, respectively. Porphyra-334 seems to be the major MAA in AFA since shinorine was present only in small quantities (peak area ratio 1:15).

Figure 7:
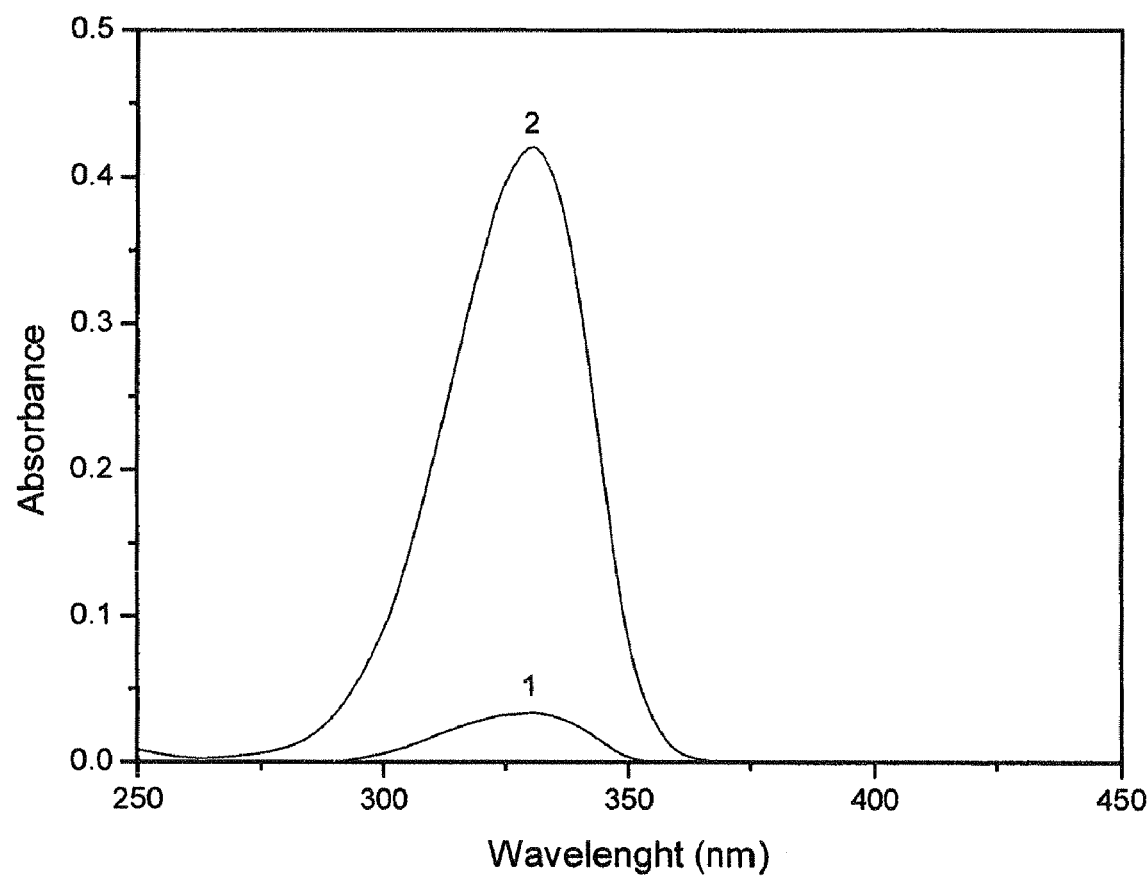
FIG. 7 shows the UV spectra of purified MAAs indicating their absorption maximum at 334 nm.

The UV spectra of the purified MAAs confirmed their absorption maximum at 334 nm (FIG. 7). Taking into account that the molar extinction coefficients at 334 nm for shinorine and porphyra-334 are of 44700 and 42300 M$^{-1}$ cm$^{-1}$, respectively, we calculated:

a) for Klamath algae, concentrations of 0.49 mg g$^{-1}$ DW for shinorine and 7.09 mg g$^{-1}$ DW for porphyra-334; the total MAA content being thus equal to 0.76% algal DW;

b) for the extract, concentrations of 17-21 mg for MAAs (that is 1.7-2.1% DW).

These are significant data, as the whole algae AFA contains high constitutive level of MAAs (0.76% DW), close to the maximal concentration found under UV exposure, i.e. 0.84% (8). Also, we found that the extract has a much higher concentration than the whole algae, reaching levels that are much higher than the maximal potential concentration.

MAAs (shinorine and porphyra-334 in the extract) are structurally simple molecules, with a molecular weight of 300. This allows these water soluble molecules to easily cross the various barriers, from the intestinal membrane to the blood-brain barrier, confirming their ability to express their antioxidant activity anywhere is needed, from the gut to the brain.

Evaluation of the Antioxidant Effect of MAAs

Figure 18:
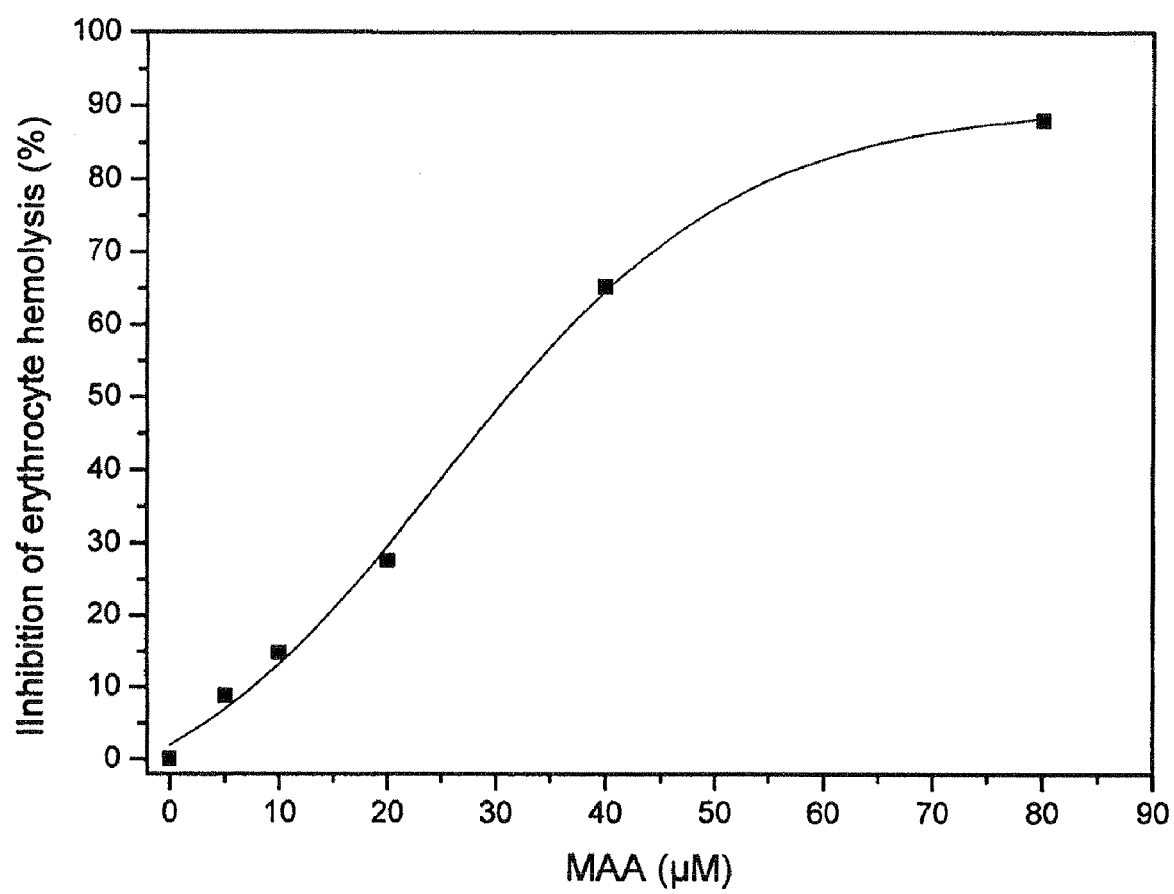
FIG. 18 shows that MAAs cause a dose-dependent reduction in erythrocyte hemolysis.

To evaluate the antioxidant properties of the MAAs contained in the extract, samples of human erythrocytes have been incubated for 3 hrs at 37° C. with increasing quantities of MAAs (5-80 μM) together with 100 mM AAPH to induce the free radical chain formation with consequent oxidation of the membrane phospholipids with parallel increase of erythrocyte hemolysis, measured by dosing hemoglobin with the Drabkin's solution (33). The results are shown in FIG. 18, where it is possible to observe how MAAs cause a dose-dependent reduction in erythrocyte hemolysis induced by AAPH, thus protecting the cell from oxidative damage.

Figure 19:
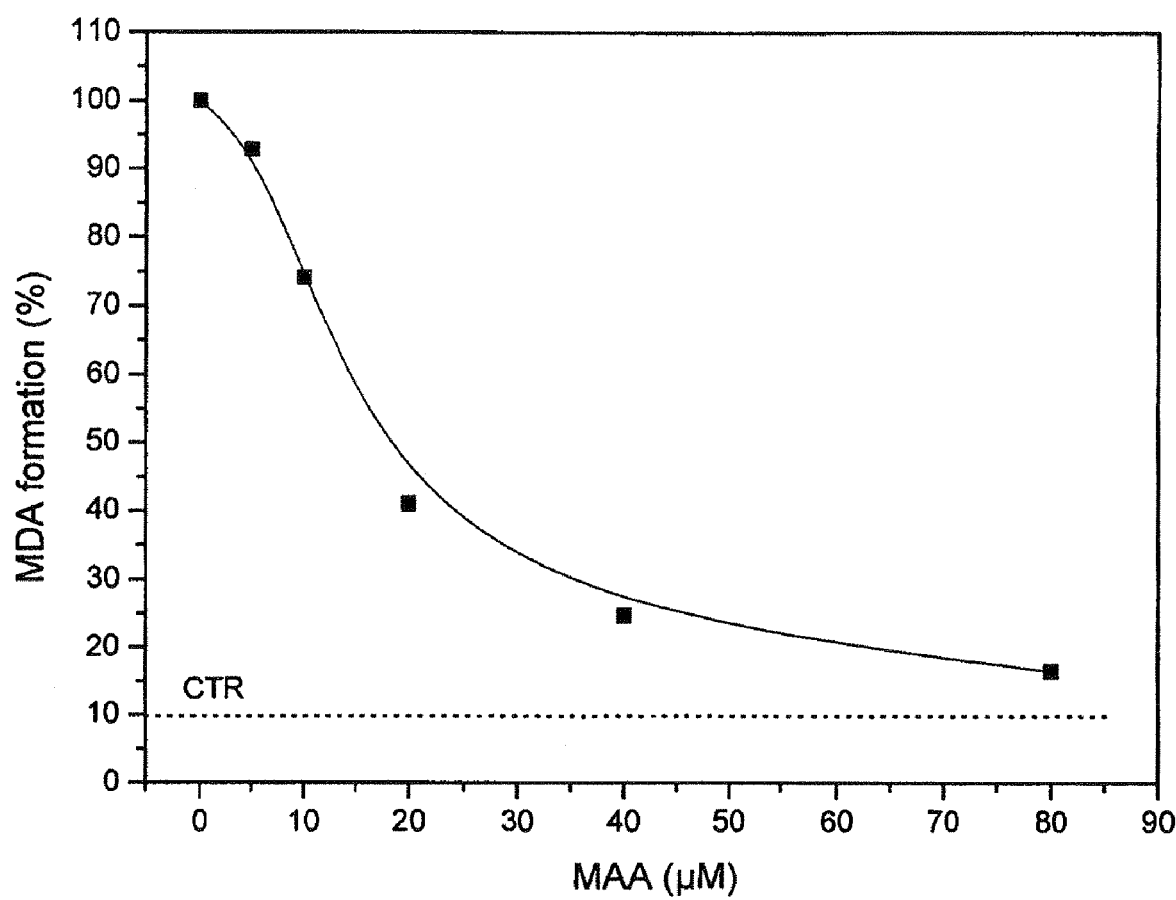
FIG. 19 shows that MAAs cause a dose-dependent reduction in MDA levels.

In the same way, the incubation of the plasma samples with oxidative agent ($CuCl_2$ 100 μM) generates increased levels of malondialdehyde (MDA), a late byproduct of lipid peroxidation which is measured through spectrophotometer at 535 nm after a reaction with thiobarbituric acid (TBA test). When plasma is incubated for 2 hrs at 37° C. with $CuCl_2$ 100 μM together with increasing quantities of MAAs (5-80 μM) extracted from AFA Klamath, it is possible to observe a dose-dependent reduction of the MDA levels, as shown in FIG. 19. With a concentration of MAAs equal to 80 μM MDA levels are obtained very similar to those of the non-oxidated plasma (control).

Both tests allows us to state that MAAs from AFA are true antioxidant molecules conferring to the extract more power as a scavenger of free radicals besides that deriving from its phycocyanins.

C) Determination of Further Synergic Factors that Make the Extract More Powerful than the Phycocyanins Contained in it.

AFA Klamath algae contain a wide matrix of nutrients endowed with different functional activities. In particular, Klamath algae and the extract contain important active principles such as chlorophyll; beta-carotene and other pro-vitamin A carotenoids; xantophyllic carotenes such as canthaxanthin; antioxidant vitamins and minerals.

Chlorophyll

In the last few years there has been a strong development in the research on a molecule, chlorophyllin (CHLN), which is a semi-synthetic analog of chlorophyll (CHL). Various studies have demonstrated significant antioxidant properties of CHLN, notably higher than the more common antioxidant (vitamins C and E, GSH, etc.), particularly in relation to essential organs such liver and brain (9). The antioxidant property is associated to a specific antinflammatory property, due to the ability of CHLN to selectively inhibit COX-2 (10). Chlorophyll's ability to selectively inhibit COX-2, together with the same ability by phycocyanins, makes the extract particularly powerful as a natural anti-inflammatory. This also helps explaining the fact, that the extract is a more powerful COX-2 inhibitor than the phycocyanins contained in it.

More generally, CHLN has shown anti-mutagenic (11). and anti-proliferative properties in relation to various types of tumor, such as those of the liver (12), breast (13) and colon (14). Since phycocyanins also have significant anti-proliferative properties, the simultaneous presence of both molecules makes the extract a potentially significant anti-tumor product.

Even though most studies have been done on the semi-synthetic CHLN, given the close similarity of the two molecules, the same properties can be attributed also to natural chlorophyll. In fact, when the anti-proliferative capacity of the two molecules has been compared, natural CHL has shown to be significantly more powerful than CHLN; and at much lower concentrations (15).

The antioxidant, anti-inflammatory and anti-proliferative synergy of phycocyanins and chlorophyll contributes to the significant superiority of the AFA Klamath extract, considering that in Klamath algae the concentration of chlorophyll is one of the highest in nature, with a minimum of 1% (as opposed to a maximum concentration of 0.3% for the vegetables richest in chlorophyll like wheatgrass and other grasses).

The method to quantify chlorophyll a in AFA algae is based on the extraction of the pigment in an organic solvent after breaking the algal cells, and the subsequent spectrophotometric determination, as discussed in the literature (16). After using different types of organic solvents, we found methanol to have the best extraction ability. The sample (100 mg of AFA REFRACTANCE WINDOW 2 MESH 122/071005) has been suspended in 10 ml of 100% methanol, homogenized through a mechanical potter for 3' and left on a rotating plate for 24 h at room temperature in the dark.

The resulting extract has been then centrifuged at 3000 rpm for 5' at 4° C.; the supernatant had been collected and dosed, while the pellet has been again resuspended in 10 ml 100% methanol for a second time extraction. After 24 h at room temperature, the extract has been centrifuged at 3000 rpm for 5' at 4° C., the supernatant has been collected and dosed, while the pellet has been again resuspended in 10 ml 100% methanol for a third time extraction. The chlorophyll a concentration in the three methanol extracts has been calculated by means of the following Porra equation (17), with the pigment having a characteristic absorption peak at 664 nm.

$$\text{Chlorophyll a (µg/ml)} = 16.29 \times Abs_{664}$$

With the first extraction, we obtained a chlorophyll a concentration of 96.11 μg/ml; with the second and third extractions, concentrations of 4.63 and 0.68 μg/ml. The total content of chlorophyll a in the AFA sample is therefore of 101.42 μg/ml, or 10.14 mg/g DW (1.014% DW).

By using the same methodology described above, we found that in the Basic Extract there is an approximate reduction of the chlorophyll content of 50%, thus with a concentration of around 0.5%.

Carotenes

Klamath algae has a high content of carotenes, expressed in beta-carotene. Moreover, it contains a wide spectrum of carotenes, both precursors and non-precursors of vitamin A. Among the non-precursors, Klamath algae has a particularly significant content of canthaxanthin:

Klamath algae Total carotenes as beta-carotene=1600 mg/Kg

Canthaxanthin=327 mg/Kg

Basic Extract Total carotenes as beta-carotene=420 mg/Kg

Canthaxanthin=41 mg/Kg

Extract B Total carotenes as beta-carotenes=2400 mg/Kg.

The above numbers are an average of different tests on different batches of product over the years. The concentration of carotenes in the Basic Extract is clearly reduced, although it remains significant. Most of all, the carotenes in the algae and its extract are highly assimilated by our organism, because they are from a natural food source which does not have any cellulose membrane nor other factors that in common vegetables partially inhibit assimilation. Plasma retinol is the active form of vitamin A, and it has shown to have important antioxidant properties, and to be able to protect various systems of our organism, from the eye to the liver, from the mouth to the nervous system (18).

Particularly interesting is the content of canthaxanthin, a carotenoid endowed with an antioxidant action higher than beta-carotene itself relative to ROS (19), and intermediate between beta-carotene and lycopene (maximum effect) and lutein and zeaxanthin (minimum effect) in relation to the singlet oxygen (20). Canthaxanthin possesses also strong anti-lipoperoxidation properties (21), synergic with the same properties of the phycocyanins and chlorophyll contained in the algae and its extract. This synergy helps explain the fact that the extract, in terms of antioxidant and anti inflammatory activity, is more powerful than the purified phycocyanins contained in it.

Testing the Basic Extract vs. AFA-Phycocyanins and PCB.

Basic Extract's Inhibition of TBARS Formation from Oxidative Damage by $CuCl_2$

Figure 20:
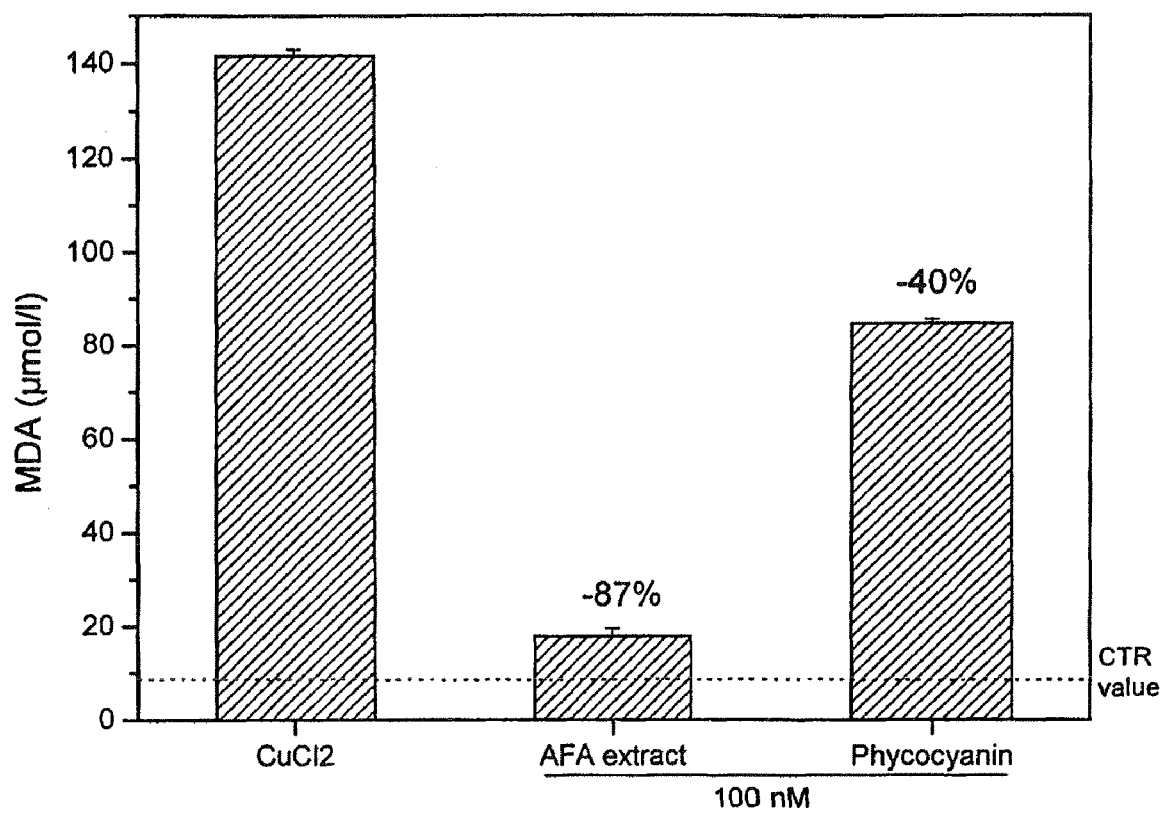
FIG. 20 shows a comparison of the effect of Basic Extract and pure phycocyanin on MDA levels.

The antioxidant power of the extract, with a standardized content of AFA's PC, has been compared also with that of the purified PC itself, as well as with that of the purified chromophore phycocyanobilin (PCB), the active prosthetic group of the PC. The tests on the malonyldialdehyde (MDA) formation generated by the oxidation of plasma with $CuCl_2$ show that the extract has a higher antioxidant power than the pure PC and its chromophore PCB, due to the presence in the whole extract of other active antioxidant molecules; while PC and PCB have a similar antioxidant capacity, with a degree of inhibition of MDA formation of 30-40% at a concentration of 100 nM, the Basic Extract, with a similar concentration of 100 nM of PC generates a degree of inhibition of up to 89% (FIG. 20).

Figure 21:
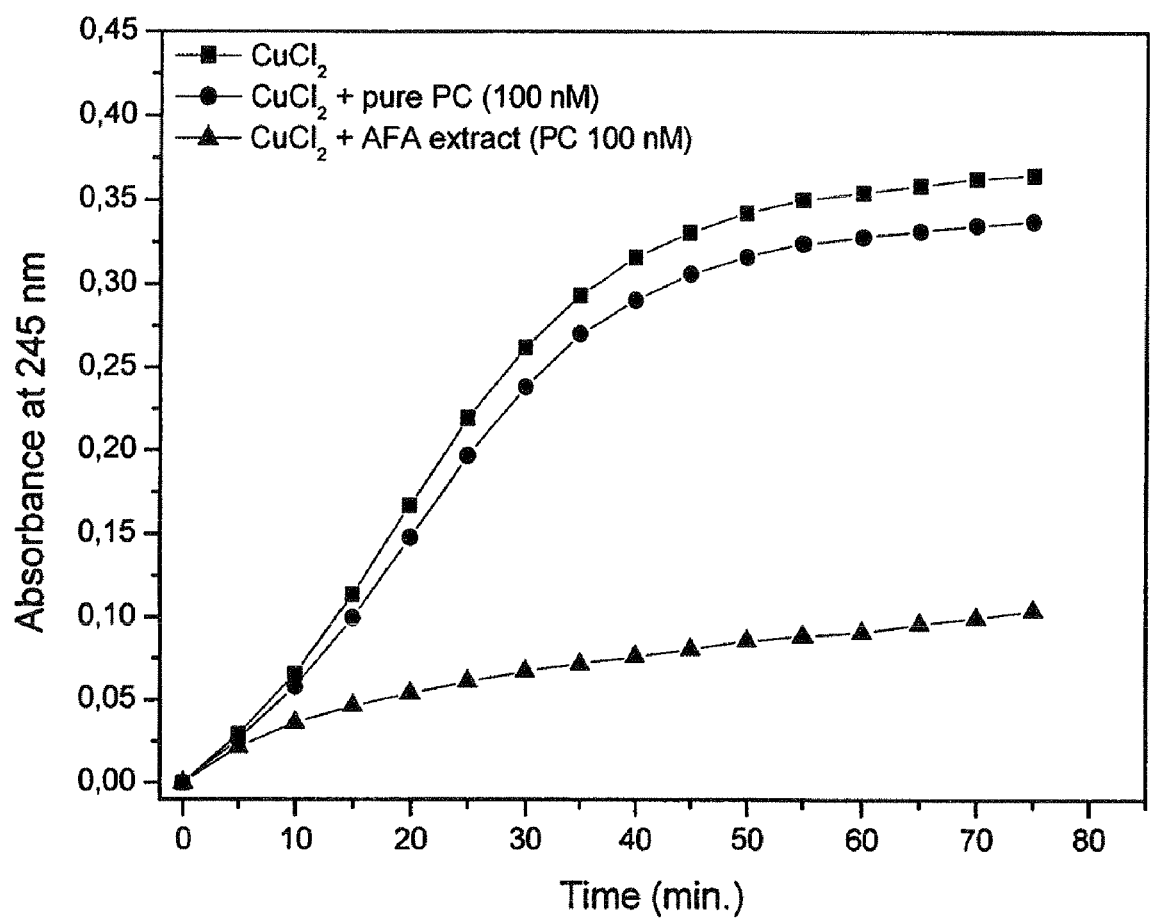
FIG. 21 shows the effect of Basic Extract and pure phycocyanin on the formation of conjugated dienes.

Also in the formation of conjugated dienes after oxidation of plasma with CuCl2 the Basic Extract at a concentration of 100 nM PC has an antioxidant capacity significantly higher than the pure PC at the same concentration of 100 nM. FIG. 21 shows indeed that, contrary to the pure PC, with the extract the formation of conjugated dienes is practically completely inhibited. Again, this shows how the Basic Extract is significantly more potent than the pure PC, clearly due to the presence in it of other active molecules, in particular the AFA-phytochrome.

Pre-Incubated Basic Extract's Inhibition of TBARS Formation from Oxidative Damage by CuCl2

Figure 22:
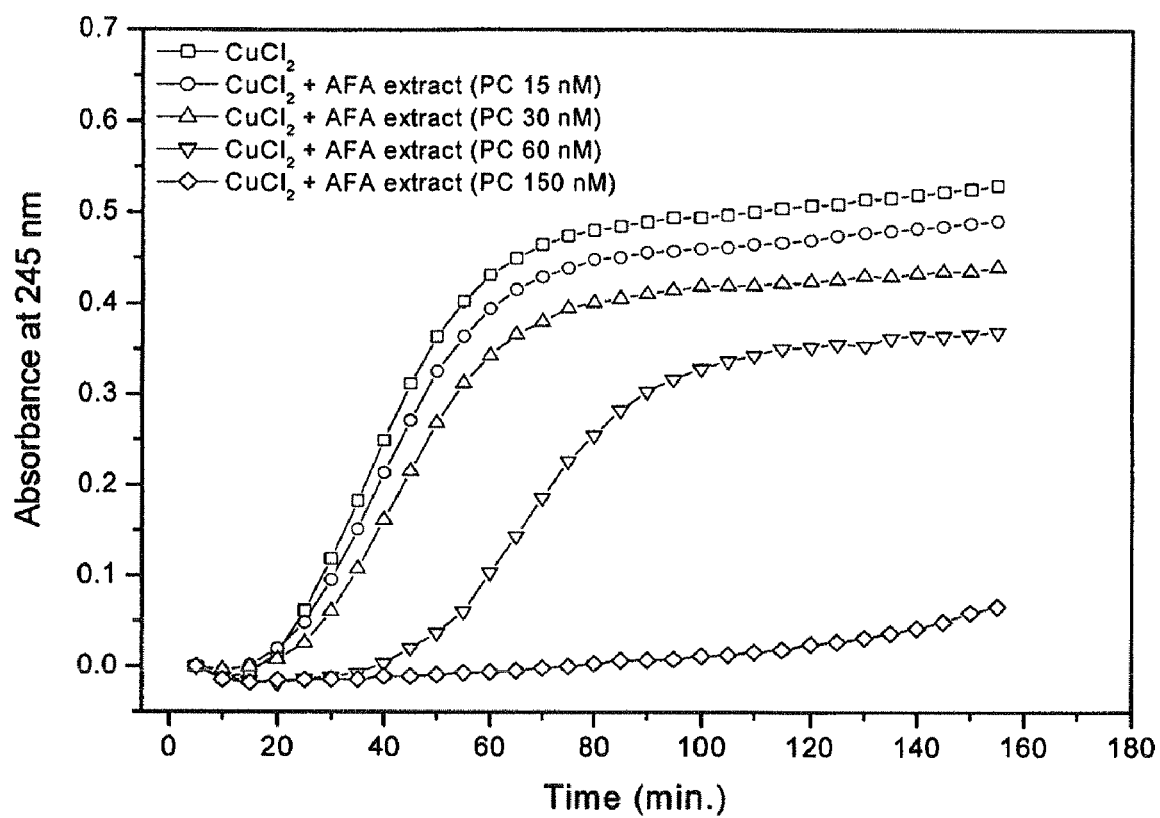
FIG. 22 shows a dose-dependent reduction in the formation of conjugated dienes caused by AFA Extract with increasing concentrations of phycocyanin.

When the AFA extract was pre-incubated with the samples of human plasma, the subsequent incubation of the same samples with the oxidative agent $CuCl_2$ at 100 µM, the oxidation of the lipoproteins, as measured by the production of the early by-products conjugated dienes through a spectrophotometer at 245 nm), was strongly reduced in a dose-dependent manner. The progressive diminution of the oxidation, oxidation which moreover develops after a first lag-phase in which the formation of dienes is inhibited by the extract, reaches a level of almost complete inhibition with a PC concentration of just 150 nM in the extract (FIG. 22).

Figure 23:
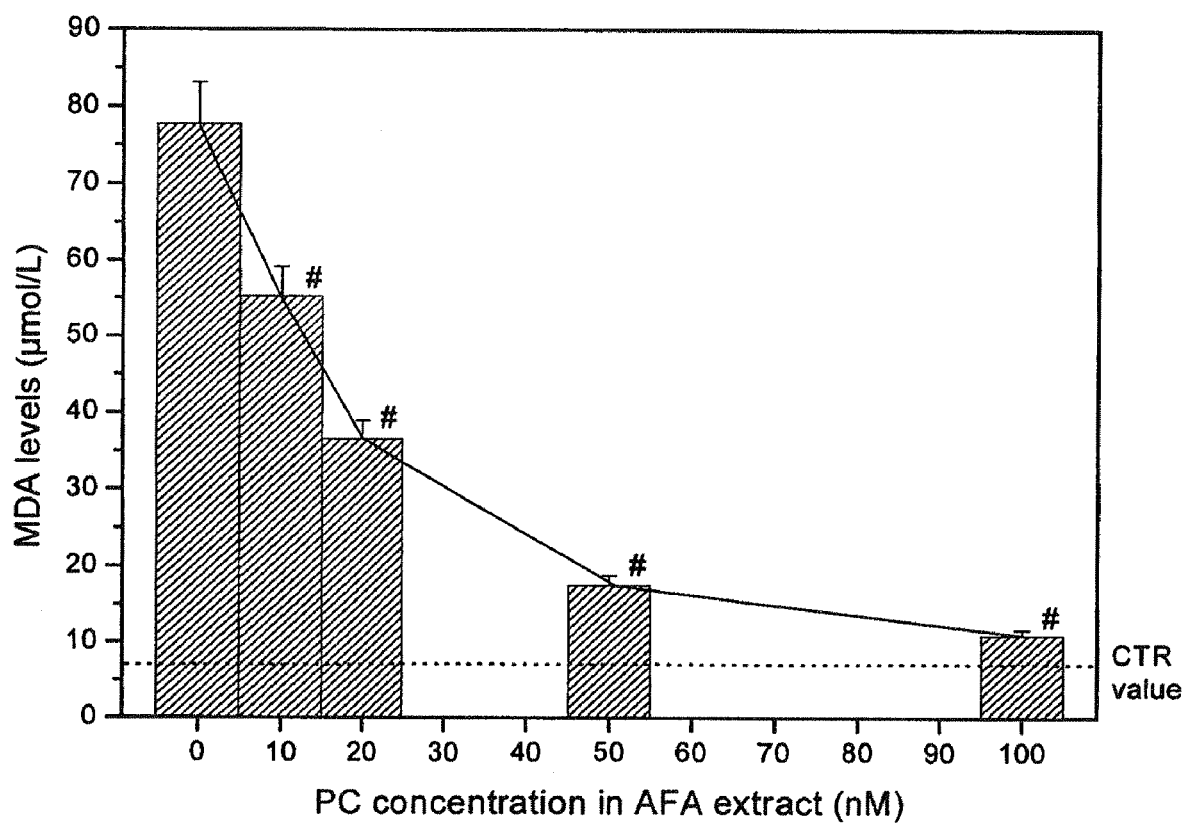
FIG. 23 shows a dose-dependent decrease in MDA levels caused by AFA Extract with increasing concentrations of phycocyanin.

The oxidation of plasma lipids with $CuCl_2$ produces also, at a later stage, the formation of malonyldialdehyde or MDA. The pre-incubation of plasma with the AFA extract also generates a dose-dependent reduction of the MDA levels, so strong that with a PC concentration of just 100 nM we obtained MDA values wholly comparable with those of non-oxidated or control plasma (# $p<0.05$) (FIG. 23).

ORAC Evaluation of the Basic Extract

To evaluate the antioxidant capacity of the extract in terms of the ORAC test, we used the same methodology we used to test the ORAC for PC and PCB. In order to test both the water soluble and the lipid soluble components of the AFA extract, we first prepared the two water and lipid soluble extracts, as follows.

Preparation of the Water Soluble Extract
Weigh 10 mg of extract in 1 ml of distilled water and homogenize for 1 min through a mechanical potter.
Centrifuge at 2500 rpm for 10' at 4° C. to remove cellular debris.
Collect the supernatant and resuspend the pellet in 1 ml of water.
Homogenize for 1 min with a mechanical potter.
Centrifuge at 2500 rpm for 10' at 4° C.
Collect the supernatant and mix with that obtained from the first water extraction.
Preserve the water extract (with a blue color for the presence of the PC) at +4 o-20° C.
Preparation of the Lipid Soluble Extract
Resuspend the pellet obtained from the previous extraction in 1 ml of acetone.
Homogenize for 1 min with a mechanical potter.
Centrifuge at 2500 rpm for 10' at 4° C.
Collect the supernatant and resuspend the pellet in 1 ml of acetone.
Homogenize for 1 min with a mechanical potter.
Centrifuge at 2500 rpm for 10' at 4° C.
Collect the supernatant and mix with that obtained from the first extraction with acetone.
Preserve the lipophilic extract (with an orange color for the presence of carotenes) at +4°-20° C.

Figure 24:
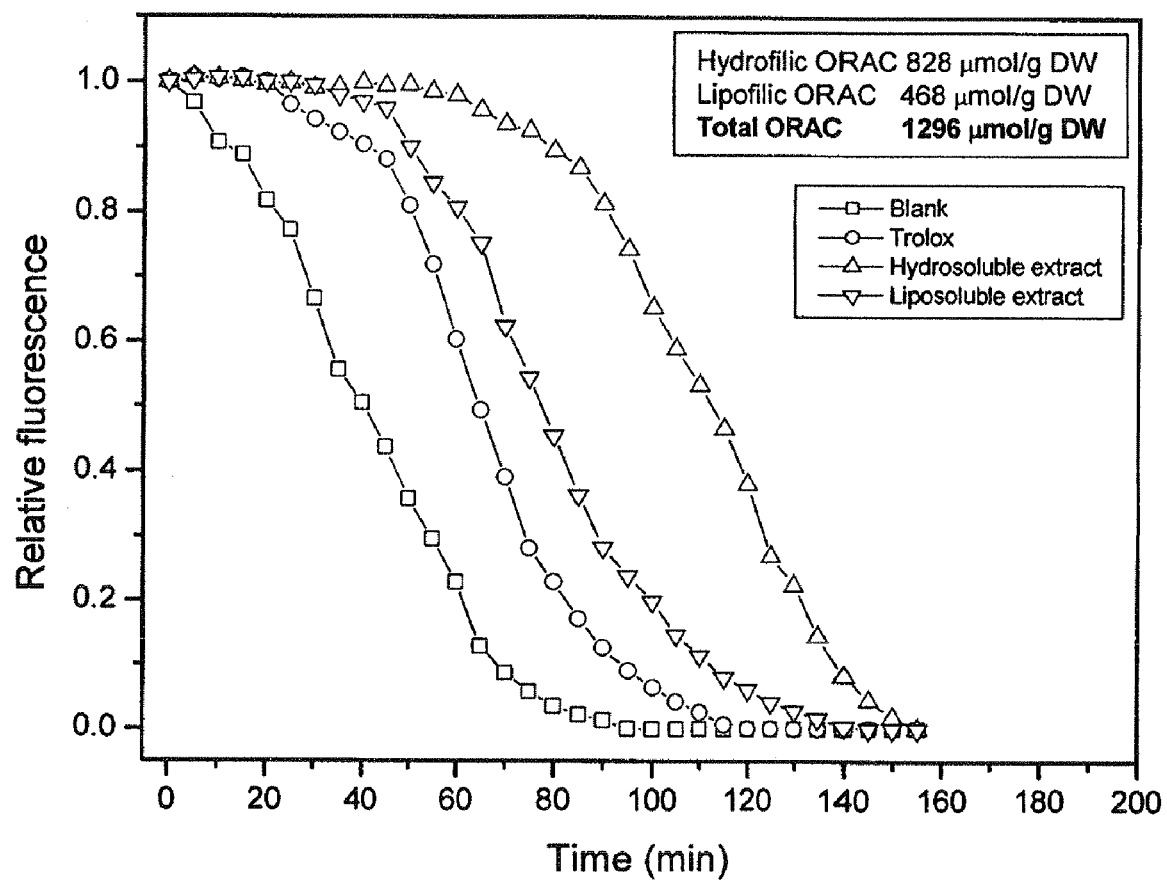
FIG. 24 shows the decay in fluorescence caused by AAPH in the absence (blank) and presence of hydrosoluble extract and liposoluble extract relative to the reference standard Trolox.

FIG. 24 shows the decay of the fluorescence caused by AAPH in the absence (blank) and presence of the two extracts relative to the reference standard Trolox. Based on the measurement of the areas under the curve, we obtained an ORAC for the water soluble extract of 828 µmol Trolox equiv/g dry weight; and for the lipid soluble extract of 468 µmol Trolox equiv/g dry weight. This means that the total ORAC capacity is of 1296 µmol Trolox equiv/g dry weight.

In Vivo Studies

Effect of the Supplementation with an AFA Algae and AFA Extract on the Plasma Levels of MDA, GSH and Retinol in Healthy Subjects.

The following study was done with a formula mostly based on AFA algae and an AFA alga extract. Even though it was also containing gastrointestinal factors such as lactobacillus acidophilus and proteolytic enzymes, the antioxidant activity is to be attributed mostly to the algal factors.

Eight relatively healthy subjects freely volunteered to participate in the study: 4 men and 4 women, age 23 to 63, whose clinical history did not show any serious previous pathology, gastrointestinal, glycemic or otherwise. None of the subjects was following any special dietary or caloric restrictions, none was vegetarian, and during the supplementation no food or lifestyle modification was suggested.

Before the study started, the participants underwent objective medical analysis and evaluation of their medical history, which for the most part showed only the presence of some of the ailments, presumably of a neurovegetative nature, commonly found in the population, such as episodes of dyspepsia, generic gastrointestinal irregularities, occasional headaches, sense of heaviness after a meal, occasional events of painful joints, some instances of premenstrual syndrome.

The nutritional formula used in the study was administered in "0" vegetable capsules, containing 500 mg of powder thus composed: AFA Klamath lake algae, 200 mg; AFA extract, 100 mg; Lactobacillus Acidophilus DDS-1 (10 bill. CFU/gr), 100 mg; fermented maltodextrines with proteolytic activity, 100 mg. Each participant, starting at day 0, has taken 9 capsules a day, 3 capsules with each meal.

The blood samples were taken in heparinized vacutainers at time 0, after 1 month, and after 3 months, and each sample was divided in two parts. One part was analyzed by the Analytical Laboratory of the Hospital of Urbino for the most common parameters: emocromocytometric exam with automatic system and COULTER principle (impedenziometric), proteic and lipidic assay with automatic system and Dry Chemistry, enzymatic test for the functioning of liver, heart and kidney, thyroid profile through automated instruments based on immunophelometric and chemiluminescence principles, lymphocytes immunophenotyping through flow citometry.

The other part of the blood sample was used to test the levels of lipoperoxidation through measurement of MDA and of the antioxidants reduced glutathione (GSH), vitamin E (.-tocopherol) and vitamin A (retinol). Blood samples have been processed through centrifugation at 3000 r.p.m. for 10 minutes at +4° C., and the plasma thus obtained has been stocked at −20° C. to be used as follows. Plasmatic MDA was measured through a spectrophotometer at 535 nm according to the TBARS (thiobarbituric acid-reactive substances) methodology (28). GSH dosage was based on the GSH ability to reduce the disulfide DTNB (5,5'-dithiobis 2-nitrobenzoic acid) (29). In its reduced form, DTNB (c.e.m. 13600 $M^{-1}$ $cm^{-1}$) develops an intense yellow color, which is measured at 412 nm. Plasma levels of α-tocopherol and retinol have been determined through HPLC (Jasco Corporation, Tokyo, Japan) as described in (30) by utilizing an Alltima C18 column (5 μm, 250 mm×4.6 mm i.d.; Alltech, Italia) preceded by an Alltech pre-column (7.5×4.6 mm i.d). The chromatographic profiles have been analyzed with the Borwin 1,5 software (Jasco Corporation, Tokyo, Japan).

Figure 25:
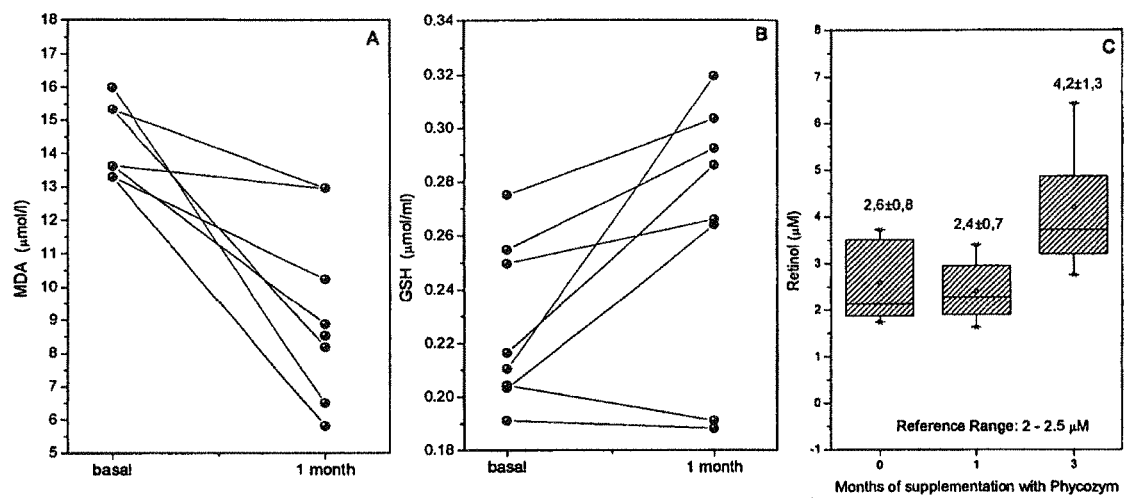
FIG. 25 shows the effect of supplementation with AFA algae and AFA extract on the plasma levels of MDA, GSH and retinol in healthy subjects.

The results obtained on the three parameters tested, concerning the oxidative/antioxidant status of the subjects, are shown in FIG. 25.

It is important the fact that the very positive results on the antioxidant status and on lipoperoxidation generated by the supplementation with the product have been obtained without introducing any dietary or lifestyle modifications. AFA-phycocyanins, phytochrome and the MAAs present in the AFA algae, and further concentrated in the AFA extract, perform also a strong positive control as a free radical scavenger, and thanks to the high level of chlorophyll, carotenoids and other antioxidant vitamins and minerals present in the AFA algae and its extract, the product proposes itself as a powerful enhancer of the general antioxidant activity in the human body.

The results can be summarized as follows:
a) there is a very high average increase in plasma retinol, namely +60% after 3 months of supplementation;
b) there is an impressive decrease in the plasma levels of MDA −35.5%), one of the most significant markers of lipoperoxidation. This result strongly confirms in vivo, the very impressive results in vitro shown above;
c) The overall antioxidant protection afforded by the product helped also the body to generate a significant increase in endogenous GSH (+16.8%).

Effects of the Supplementation with an AFA and AFA Extract-Based Product on Patients Undergoing Hyperbaric Treatment.

The hyperbaric oxygen therapy is used successfully for the treatment of several clinical conditions, such as decompression derived illnesses, carbon monoxide intoxications, gaseous embolisms and tissue infections. The exposition to hyperbaric oxygen, indeed, generates a favorable increase of the oxygen dissolved in the blood. Yet, together with a beneficial action, there can also be an increase of the circulating ROS (reactive-oxygen species) which can damage cells and tissues, if not protected by sufficient antioxidant defenses (34). This is why patients undergoing hyperbaric therapy are generally supplemented with antioxidant vitamins.

To evaluate the effects of the AFA and AFA Klamath extract-based formula on the oxidative stress induced by hyperbaric therapy, 9 patients of the "Centro di Terapia Iperbarica" of Fano (Italy) have been enrolled in the study. Among the 9 patients there were 5 males and 4 females, between 16 and 73 years of age, and affected by different pathologies like aseptic osteonecrosis of the femur (n=5), rheumatic polymyalgia (n=1) and femoral and tibial osteomyelitis (n=3).

These patients have been supplemented with the same product described above. Starting from the first hyperbaric session, the patients have started taking 6 capsules a day divided among the three main meals.

The collection of the blood samples from each patient has been performed immediately before and after the $1^{st}$ and the $15^{th}$ hyperbaric session. The samples have then been evaluated for their content of some oxidation markers, such as MDA, carbonyls, AOPP, as well as plasma thiols, liposoluble vitamins and the total antioxidant level of the plasma itself.

Figure 26:
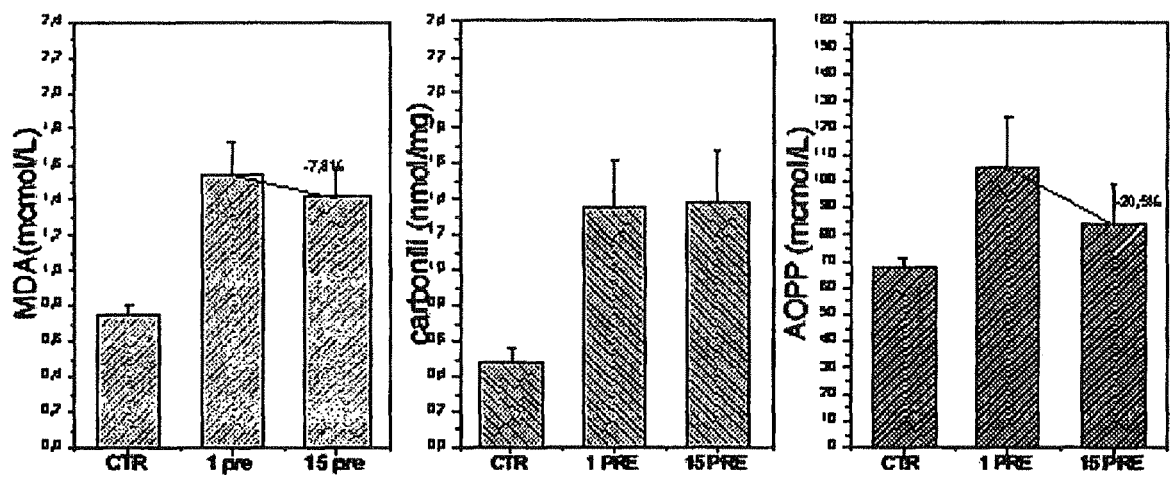
FIG. 26 shows the effect of supplementation with an AFA and AFA extract-based product on the plasma levels of MDA, carbonyls, and AOPP in patients undergoing hyperbaric treatment.

The results show that in the patients supplemented with the formula the hyperbaric treatment does not generate any increase in the oxidative markers even after 15 sessions (FIG. 26) In fact, considering that there is usually a significant increase in those markers with progression of the therapy, here we actually see a 7.8% decrease, from the $1^{st}$ to the $15^{th}$ session, of the MDA levels (lipoperoxidation), with values moving from 1.54±0.17 μmol/l ($1^{st}$ session) to 1.42±0.16 μmol/l ($15^{th}$ session) (p<0.05); a 20.5% decrease of the AOPP (late byproducts of the oxidation of proteins), with values moving from 105.7±18.8 μmol/l ($1^{st}$ session) to 84.0±15.5 μmol/l ($15^{th}$ session) (p<0.05); while the protein carbonyls (early byproducts of the oxidation of proteins) remain unchanged (FIG. 26).

Figure 27:
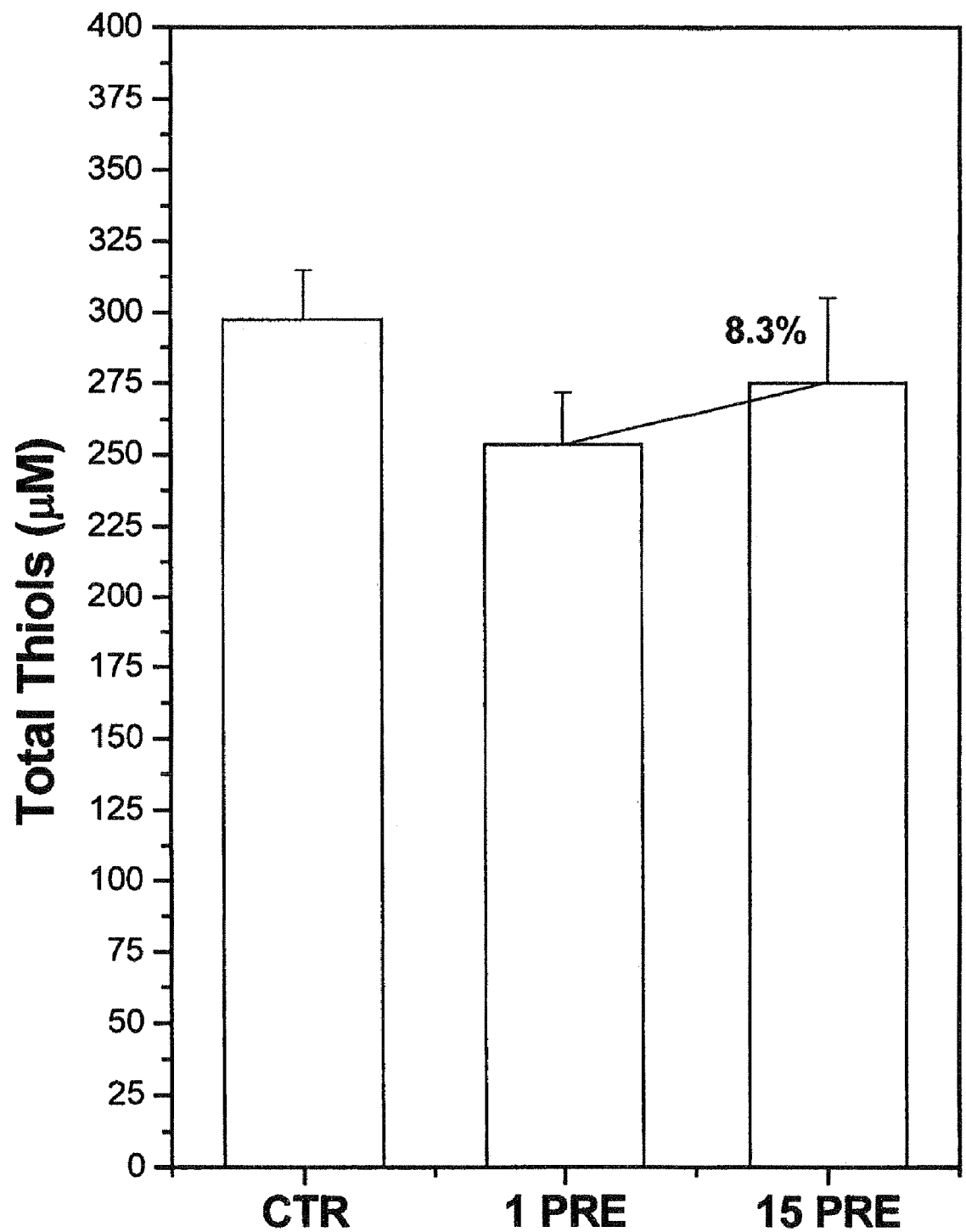
FIG. 27 shows the effect of supplementation with an AFA and AFA extract-based product on the plasma levels of total thiols in patients undergoing hyperbaric treatment.
Figure 28:
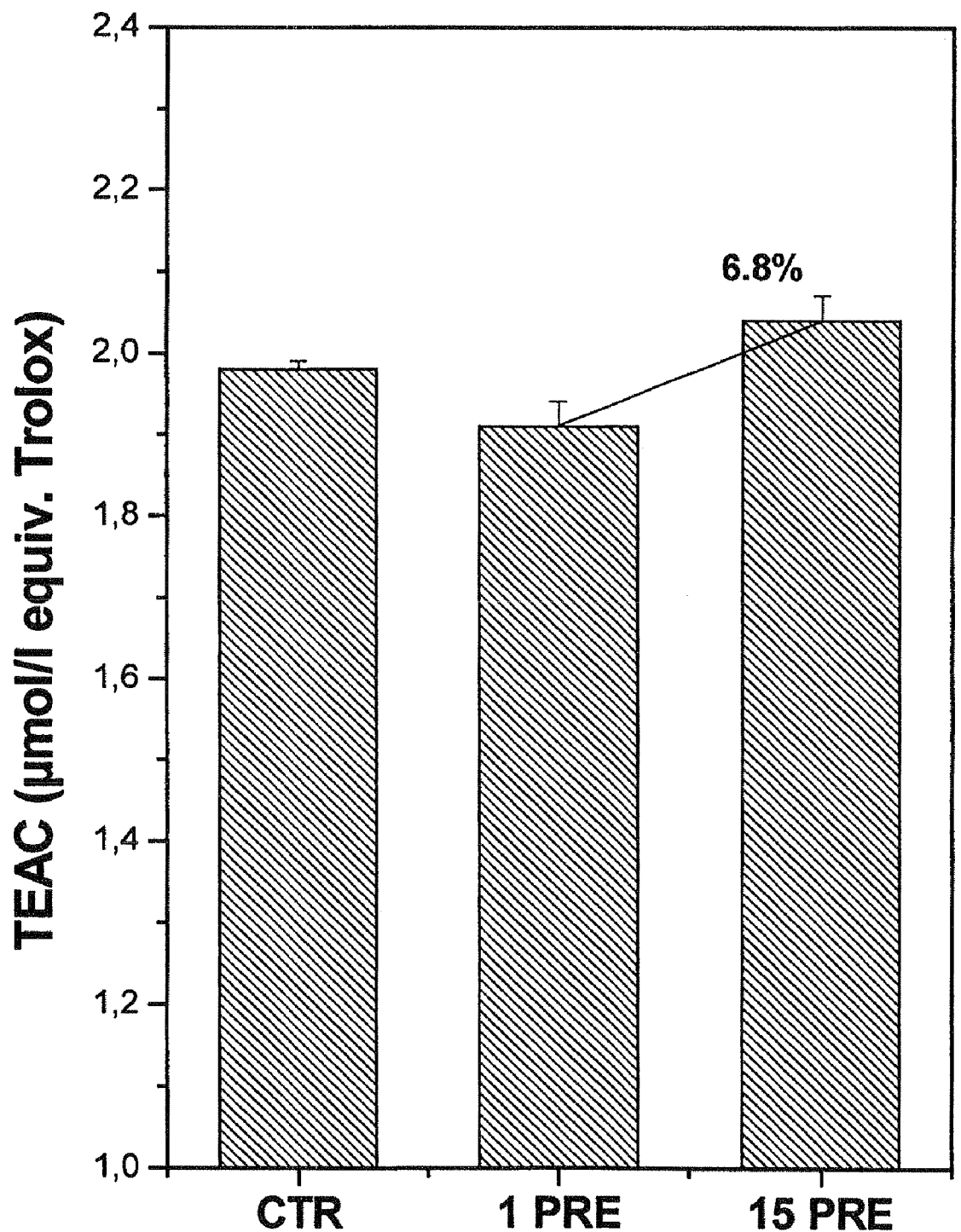
FIG. 28 shows the effect of supplementation with an AFA and AFA extract-based product on the plasma levels of TEAC in patients undergoing hyperbaric treatment.

The general antioxidant profile too is maintained during the hyperbaric treatment. The plasma levels of the total thiols (SH groups of glutathione and proteins) increase 8.3% (p=n.s.), with values that move from 254±18 μmol/l ($1^{st}$ session) to 275±30 μmol/l ($15^{th}$ session). At the same time we see a significant increase (p<0.05) of the total antioxidant status of the plasma, with values moving from 1.19±0.03 mmol/l Trolox equivalents ($1^{st}$ session) to 2.04±0.03 mmol/l Trolox equivalents ($15^{th}$ session), as shown in FIGS. 27 and 28.

Given that the plasma levels of the most common antioxidants (tocopherols, carotenoids, retinol) remain unchanged, we can suppose that the increase in the total antioxidant status is due partly to the replenishment of the antioxidant consumed, such as carotenoids and retinol, by the same nutrients provided by the formula; and by the parallel accumulation in the circulatory system of specific algal antioxidants such as phycocyanins, phytochrome, MAAs and chlorophyll. Altogether, the AFA and AFA extract based formula greatly increases antioxidant defenses, efficiently protecting the patients undergoing hyperbaric therapy from the increase of free radicals produced by hyperbaric oxygen.

Antiinflammatory Activity

In vitro Studies.

Cyclooxygenase enzymes (COX) catalyze the first step in the synthesis of eicosanoids such as prostaglandins (PG), thromboxanes and prostacyclins. There are two different isoforms of this enzyme: COX-1 is involved in the normal regulation of homeostasis; whereas COX-2 is responsible for the production of PGs, which in turn promote acute inflammation.

Phycocyanins from blue-green algae have a powerful antinflammatory activity. It has been shown that phycocyanins from the microalga *Spirulina Platensis* are efficient selective inhibitors of COX-2 (35), and that they inhibit in a physiological and partial manner the cascade that from the fatty acids leads to the formation of inflammatory eicosanoids (36).

Figure 29:
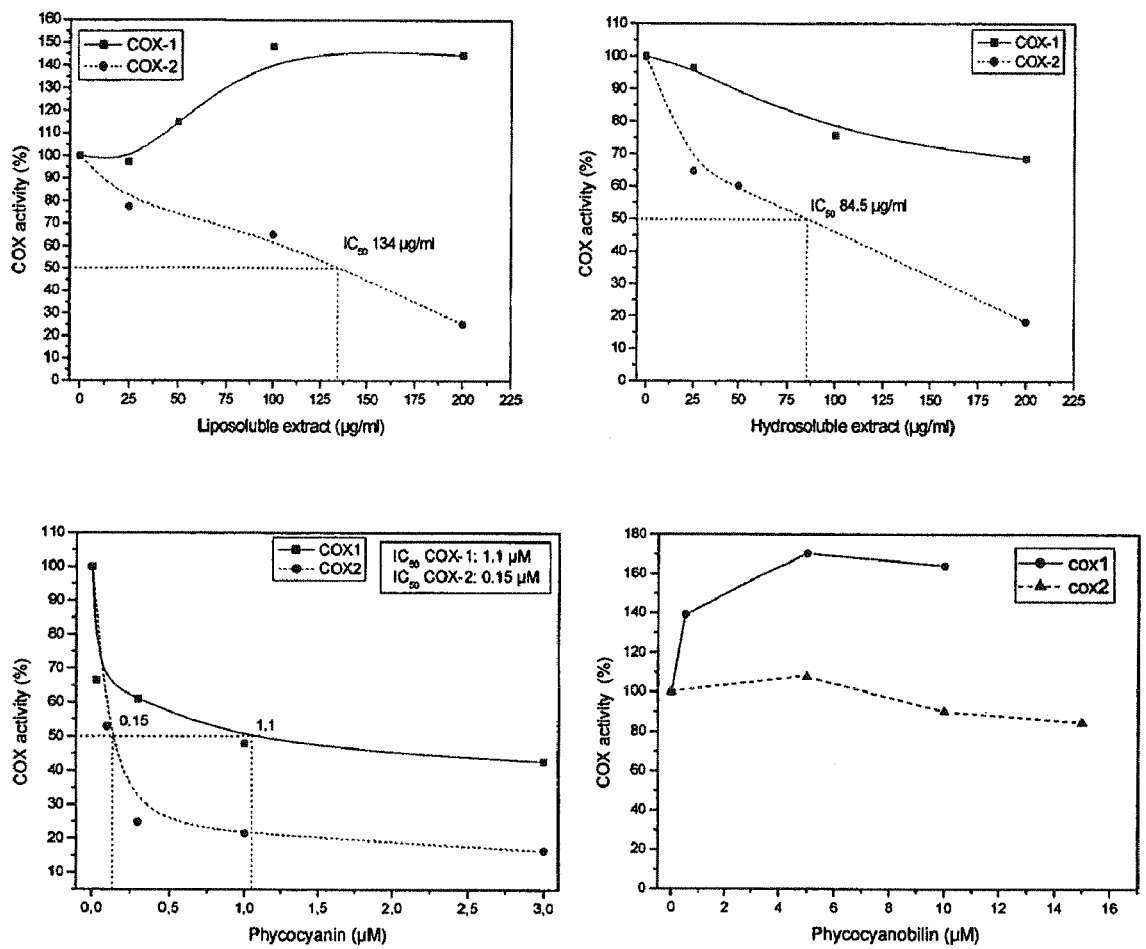
FIG. 29 shows the effect of Liposoluble Extract, Hydrosoluble Extract, phycocyanin, and phycocyanobilin on the cyclooxygenase (COX) activity.

Given that the phycocyanins from Klamath AFA algae are different from the ones from *Spirulina*, ands that no test has ever been done on their effect on the COX enzymes, we decided to perform such test through the immunoenzymatic kit "COX Inhibitor Screening Assay" of the Cayman company. We thus evaluated the COX-1 and COX-2 inhibition by the AFA extract (both the water soluble part in water, and the lipid soluble in acetone; range 25-200 μg/ml); by the pure PC (0.03-3 μM) and PCB (0-15 μM). The results are shown in FIG. 29, presenting the graphic of the percent activity of COX-1 and COX-2 at the different concentrations of AFA extract, PC and PCB.

The liposoluble fraction of the AFA Basic Extract selectively inhibits COX-2 with an $IC_{50}$ of 134 μg/ml, while the COX-1 increases. The water-soluble fraction too selectively inhibits COX-2 with an $IC_{50}$ of 84.5 μg/ml; whereas the COX-1 is only moderately inhibited (30% inhibition for 200 μg/ml of AFA extract).

The pure PC acts on both enzymes, but even in this case the inhibition is preferential for the COX-2 relative to the COX-1, being the activity on the COX-2 almost 10 times higher than that on the COX-1 ($IC_{50}$ 0.15 vs. 1.1 μM). Finally, the chromophore PCB increases the COX-1 activity and is scarcely inhibitor of the COX-2.

We thus confirmed that also the phycocyanins of AFA Klamath algae are powerful antinflammatory molecules, capable of a significant selective inhibition of COX-2. It is also interesting to notice that the COX inhibition is produced not only by the water soluble extract, containing phycocyanins, but also by the lipid soluble extract, thus indicating that other molecules present in the AFA extract.

Here we can also propose some comparative considerations with the studies that have been performed on the phycocyanins from *Spirulina*. In the study by Reddy et al., the $IC_{50}$ for the phycocyanins from *Spirulina Platensis* is reported to be 0.18 μM, against the 0.15 μM of the phycocyanins from Klamath. Apart from this slight difference in favor of the Klamath PC, there is a further and more relevant difference to underline. At 1 μM the phycocyanins from *Spirulina* generate a COX-2 inhibition around 60%; while the phycocyanins from Klamath, at the same concentration of 1 μM, generate an inhibition of around 75%. This is a substantial difference, showing that AFA phycocyanins can generate faster and more profound antinflammatory effects.

Also, the percentage of inhibition produced by AFA phycocyanins is midway between the lower level of *Spirulina*'s PC and the higher level of drugs such as celecoxib and rofecoxib (37). This means that the degree of COX-2 inhibition produced by Klamath algae's PC is ideal: high enough to produce a fast and effective antinflammatory activity, yet still partial and thus physiological to avoid the typical cardiovascular side effects of the drugs.

Also very relevant is the COX-2 inhibition activity of the AFA extract. As shown by the figures, the liposoluble component has a significant degree of inhibition ($IC_{50}$ 134 .g/ml), even though lower than that of the water soluble component, together an activity of promotion of the COX-1. This creates and interesting result, because if the inhibition of the COX-2 reduces the production of inflammatory eicosanoids, the stimulation of the COX-1 increases the endogenous production of the antinflammatory eicosanoids, thus doubling the total antinflammatory effect. This makes the liposoluble fraction of AFA Basic Extract a unique antinflammatory agent, endowed with important pharmacological properties. The present patent also protects the nutritional and pharmacological use of any liposoluble extract from Klamath algae.

If then we look at AFA Basic Extract as a whole, the combined activity of the water soluble and lipid soluble components generates a significant inhibition of the COX-2, given that both act as powerful COX-2 inhibitors; and a substantial maintenance of the same level of the COX-1, resulting from the reduction of the COX-1 produced by the water soluble component on the one hand (−30%), and the stimulation of the COX-1 produced by the liposoluble component (+45%). The $IC_{50}$ for the AFA extract as a whole is around 100 .g/ml (the average of the two components), while at the dosage of 200 .g/ml there is a COX-2 inhibition of approximately 75%. This is the level of per cent inhibition discussed above in relation to the pure PC, and the consideration presented there acquire a particular meaning in light of the fact that 200 .g/ml in vitro can plausibly correspond to an in vivo dosage of just 600-800 mg (38). Even while waiting for experimental confirmations, we can plausibly state that the AFA extract, at dosages easily reached with just 1-2 capsules/tablets a day, constitute a powerful antinflammatory agent, endowed of therapeutic properties, nutriceutical and pharmacologic, really unique. These properties have been confirmed by an in vivo animal study.

In vivo Study

Figure 30:
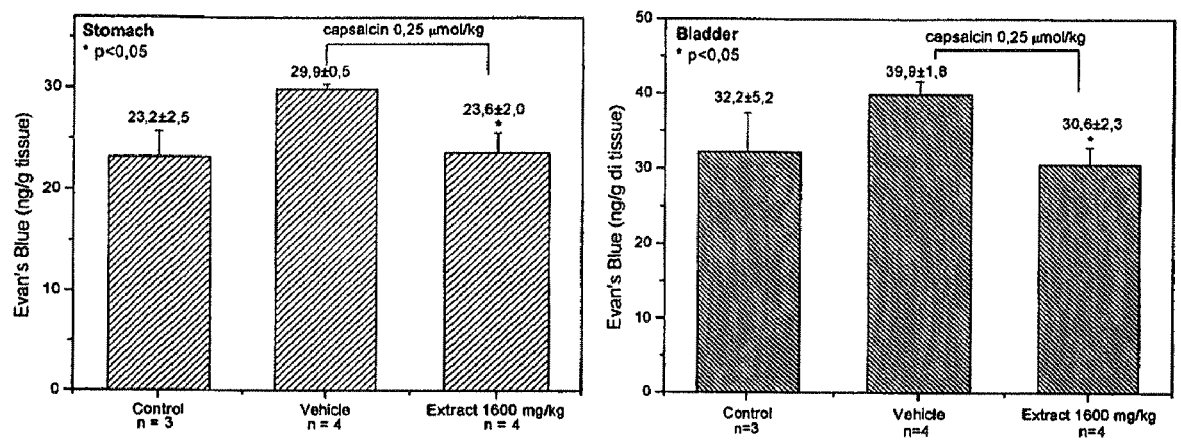
FIG. 30 shows that AFA extract inhibits the outflow of plasma in stomach and bladder of mice injected with 0.25 µmol/kg capsaicin.

In this study we investigated the antinflammatory properties of an algal extract containing PC (AFA extract) in male Swiss albino mice subjected to a pro-inflammatory stimulus with capsaicin 0.25 .mol/kg (the active principle of chili pepper) or with substance P 2 nmol/kg (acting with the receptors responsible for the inflammatory neurogenic response). The tissues inflammation levels have been measured through a spectrophotometric dosage of the coloring agent Evan's Blue accumulated in the inflammation sites as a consequence of the outflow of the plasma proteins in the tissues. As shown in FIG. 30, the intravenous injection of capsaicin (0.25 .mol/kg) or SP (2 nmol/kg) induces and increase in the outflow of plasma in the examined tissues relative to that observed in the control mice not subjected to the inflammatory stimulus. The pretreatment of the mice with the AFA extract (1600 mg/kg or 800 mg/kg) significantly inhibits the outflow of plasma, bringing it down to values equal to the control group.

Indeed, the injection of capsaicin induces an increase of plasma outflow both in the stomach (23.2±0.2 vs. 29.9±0.5 ng EB/g of tissue, $p<0.05$) and in the urinary bladder (33.2±5.2 vs. 39.9±1.8 ng EB/g of tissue, $p<0.05$). The pretreatment of the mice with 1600 mg/kg of AFA extract induces a significant decrease of plasma proteins outflow in both tissues, with values of 23.6±0.2 ng EB/g in the stomach and 30.6±2.3 ng EB/g in the urinary bladder.

Figure 31:
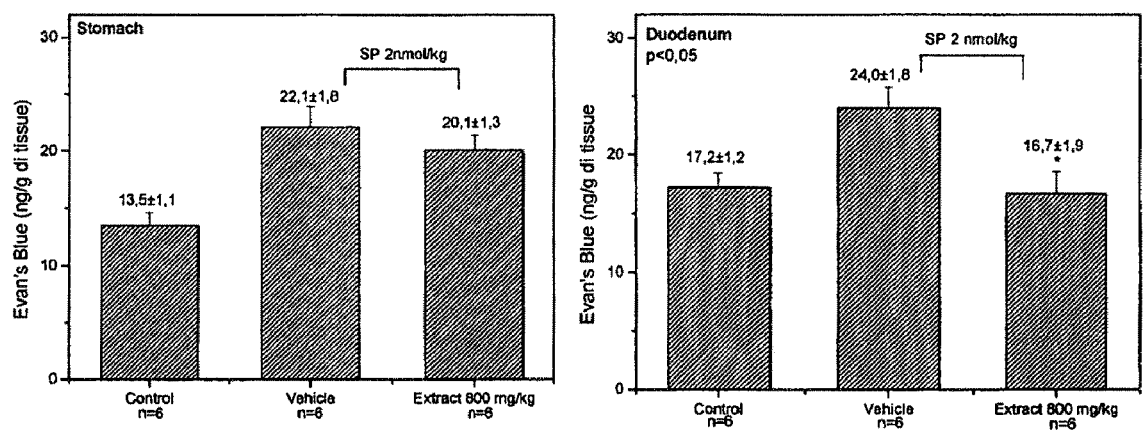
FIG. 31 shows that AFA extract inhibits the outflow of plasma in stomach and duodenum of mice injected with 2 nmol/kg of SP.

In a similar way, the injection of SP induces a significant increase of plasma outflow in the stomach (13.5±1.1 vs. 22.1±1.8 ng EB/g of tissue, $p<0.05$) and in the duodenum (17.2±1.2 vs. 24.0±1.8 ng EB/g of tissue $p<0.05$). The pretreatment of mice with 800 mg/kg of AFA extract decreases the plasma proteins outflow with values of 20.1±1.3 ng EB/g in the stomach (p=n.s.) and 16.7±1.9 ng EB/g in the urinary bladder (p<0.05) (FIG. 31).

Antiproliferative Activity

In the literature it has been reported that the pure PC from the microalga *Spirulina* possesses in vitro a significant property to inhibit the growth of tumor cellular lines such as the leukemia cell lines (39) and the macrophagic cellular lines (40), through an apoptotic mechanism.

Figure 32:
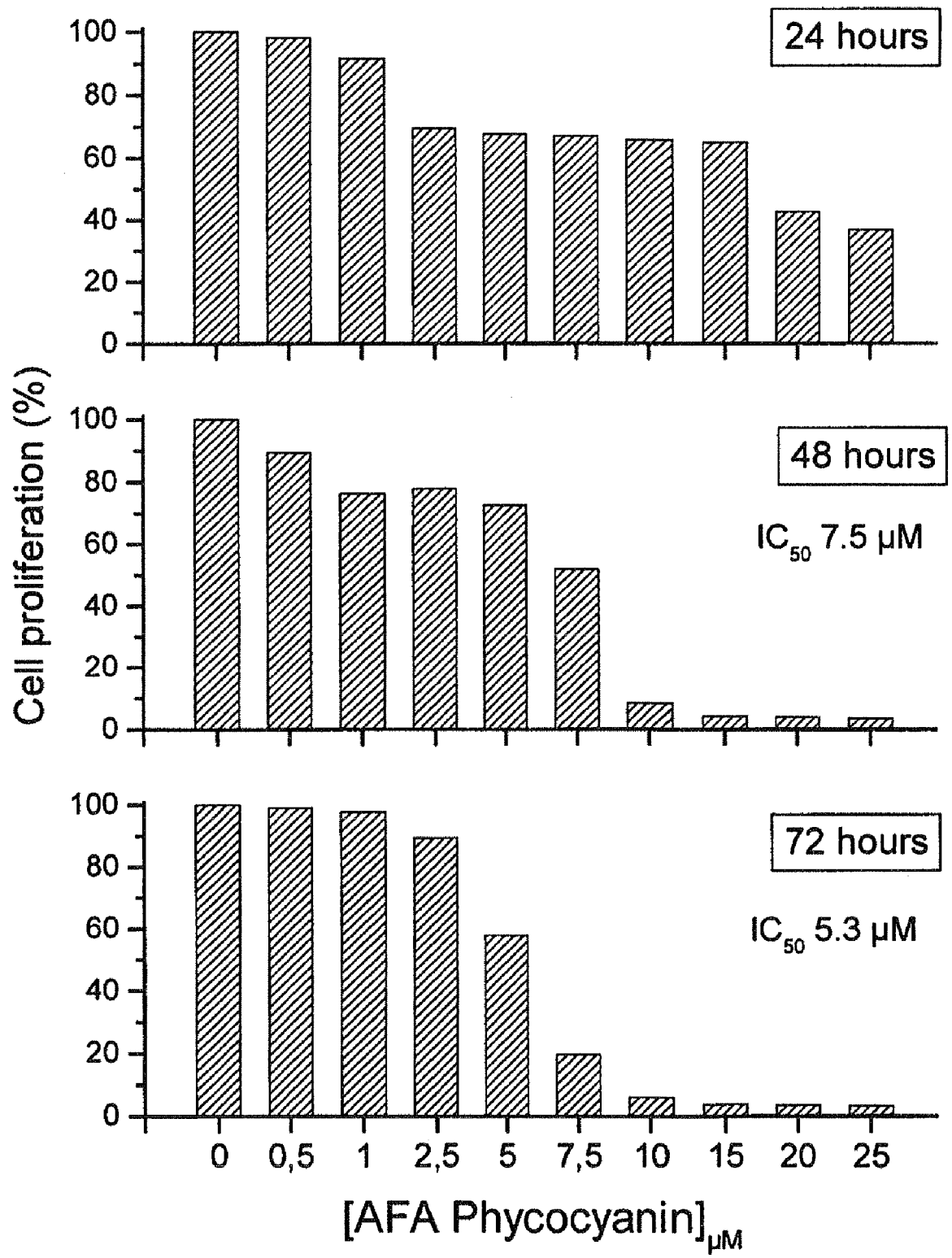
FIG. 32 shows that AFA-PC shows a dose and time dependent anti-proliferative effect.

We then tested the antiproliferative activity of pure AFA-PC, with its C-PC/PEC complex, on the monocyte-macrophagic RAW 264.7 tumor cell line by incubating the cells with increasing dosages of PC (range 0-25 μM). The analysis of the vitality of the cells after 24, 48 and 72 hrs. of incubation has shown that AFA-PC has a very significant dose and time dependent antiproliferative effect, as results from FIG. 32.

AFA Extract's Dermatological and Cosmetic Properties

Given the antioxidant and antinflammatory properties of the phycocyanins and other synergic molecules in AFA Klamath algae and its extracts, it is evident that, beside the oral administration for nutritional and pharmacological purposes, they can also be used topically on the skin, both for dermatological therapeutic uses and for cosmetic purposes.

Occlusive Patch Test (Irritation Test)

As a preliminary study, we tested Klamath AFA algae toxicologically, to establish that its dermatological use does not create any toxic or inflammatory reaction. The test has been performed at the "Centro di Cosmetologia" of the University of Ferrara, Italy. The "occlusive patch test" has been performed in order to evaluate the irritant effect of the cosmetic product when applied in a single dose to the intact human skin. The test has been run on 20 healthy volunteers of both sexes, which have given a written consent to the experimentation. The following subjects have been excluded from the test:

all subjects who participated in similar tests in the last two months;

all subjects affected by dermatitis;

all subjects with a history of allergic skin reaction;

all subjects under anti-inflammatory drug therapy (either steroidal or non-steroidal).

The test has been performed on the powder of AFA Klamath algae. To prepare the product for application, the powder has been mixed with distilled water and directly applied into a Finn chamber (Bracco) by using a syringe; then, it has been applied lo the skin of the forearm or the back of the participants protected by a self-sticking tape. The cosmetic product was left in contact with the skin surface for 48 hours, asking the participants not to wash the area where the product had been applied for the next 48 hours. Removal of the Finn chamber and cleaning of the skin area from residual cosmetic product was carried out by the experimenter. The evaluation of skin reactions was performed 15 min and 24 hours after the removal of the Finn chambers, according to the following scale:

Erythema: 0—Absent 1—Light 2—Clearly visible 3—Moderate 4—Serious

Edema: 0—Absent 1—Light 2—Clearly visible 3—Moderate 4—Strong

The sum of erythema and edema score is defined "irritation index". Irritation index values at 15 min. and 24 hours are recorded in the final report. The average irritation index of the 20 tests is calculated. The product was then classified according to the following parameters:

| Average irritation | |
| --- | --- |
| INDEX | CLASS |
| <0.5 | non irritating |
| 0.5-2.0 | slightly irritating |
| 2.0-5.0 | moderately irritating |
| 5.0-8.0 | highly irritating |

The results of the test on AFA Klamath algae, according to the methodology and parameters described above are:

"The tested product, applied diluted with distilled water (1:10) under occlusive conditions on the healthy skin of 20 volunteers resulted in a mean index of irritation of:

0.25 (zero. twenty five) 15 minutes after the removal of the Finn Chamber 0.15 (zero. fifteen) 24 hours after the removal of the Finn Chamber.

According to the evaluation scale used, the product Klamath Algae (*Aphanizomenon Flos Aquae*) can be classified as: not irritating".

Efficacy Study

Once ascertained the non irritating and non toxic nature of the algae as a cosmetic and dermatological ingredient, we proceeded to prepare a cream containing 8% of the Klamath algae Basic Extract, to test its efficacy on cosmetic parameters such as skin elasticity, hydration and wrinkles. The test was conducted randomly on 15 individuals age 30 to 65. They were not chosen for specific dermatological or skin problems, and in fact on parameters such as volume of wrinkles the fact that most participants did not have serious wrinkles made the result statistically insignificant. Nevertheless, the results on wrinkles reduction, when wrinkles were actually present, was quite clear. The study, although not final on some parameters for lack of statistical significance, it is a preliminary report that strongly confirms the dermatological and cosmetic properties of the AFA extract, and which thus warrants further studies more clearly oriented to specific dermatological and skin problems. Here we present the methodology and main results of the study.

The test was performed comparing a product with 8% AFA extract with a placebo product constituted by the same vegetable base, but without the algae extract. We will call the two products:

a) Vegetable emulsion with AFA extract b) Basic vegetable emulsion.

15 volunteers of female sex, with an age between 30 and 65 years old have been selected for the test, following the under mentioned inclusion criteria:

good state of general health;

no dermatopathies;

no pharmacological treatment in progress;

promise not to change the usual daily routine;

no atopy in the anamnesis.

The two products were applied by the participants themselves every day, one for each side of the face, as follows:

on the right side of the face (DX): vegetable emulsion with AFA extract;

on the left side of the face (SX): basic vegetable emulsion.

The parameters that have been analyzed for this study were:

Skin elasticity

Moisturization index

Skin profilometry

The measurements of the parameters were done according the following scheme:

before product application (T0)

after 15 (T15) and 30 (T30) days of products application.

Skin Elasticity

Skin elasticity was measured by means of CUTOMETER® SEM 575 (COURAGE+KHAZAKA electronic GmbH). The measurement of the elasticity has been done on a scale of 0 to 1, 1 representing the maximum elasticity possible.

Skin Moisturizing Index

The measurement of the skin moisture is based on the internationally recognized CORNEOMETER®. A healthy skin in normal room condition (20° C. and 40-60% air humidity) in the tested region should have a moisturizing index >50. moisturizing index in the range 35-50 reveals a dry skin, while inferior by 35 a very dry skin. These values are only indicative for the interpretation of the results.

Skin Profilometry

Figure 33:
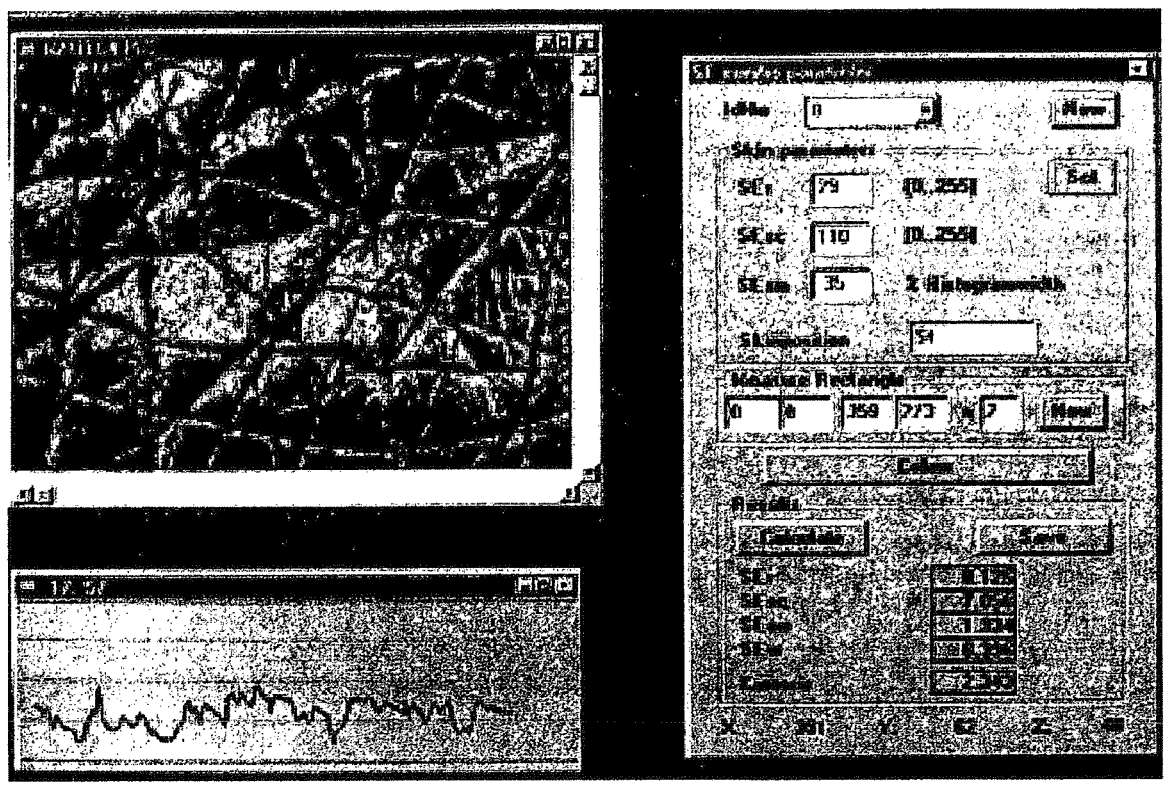
FIG. 33 shows an in vivo analysis of skin surface upon application of a cream containing 8% Basic Extract of AFA Klamath.

By means of VISIOSCAN VC 98 for the in vivo analysis of skin surface it is examined the reduction of the wrinkles (FIG. 33). The parameters are:

SEr: roughness;

SEsc: scaliness;

SEsm: smoothness, is proportional to width and form of the wrinkles;

Sew: wrinkles, is proportional to number and width of the wrinkles;

Volume: is proportional to the wrinkles depth, the deeper wrinkles are, the bigger is the volume parameter.

When the results on the various parameters were analyzed statistically through a multifactorial variance analysis (ANOVA) performed with the specific software Statgraphic plus (version 5.1), only for two parameters, namely skin elasticity and skin moisturization, statistically significant results were obtained. The conclusion that was reached by the researchers of the University of Pavia who performed the test under our instructions, was the following: "The use of the active product, applied on the right side of the face, caused a statistically significant increase of moisturization and elasticity, relative to the baseline values; whereas the treatment with placebo (left side), did not generate significant variations during the whole period of treatment."

As for the above conclusion, there was no statistically significant result on the skin profilometry. However, this was due not to a failure of the product, but to the fact that most of the participants had starting conditions, at time 0, that made it impossible, given that their skin was already close to an optimal condition, any serious improvement. This has been the weak point of the study. However, when we made a selection of the participants who actually had a skin condition in need of improvement (without falling into a condition of dermatological pathology), and interpreted the results accordingly, we obtained the following results.

Skin Elasticity

Out of 15 participants, only 12 had elasticity conditions that were less than optimal. In fact, given an elasticity index of 0 to 1 (1 being the maximum possible), we had a range of values among the participants from 0.57 to 0.98. On the base of this range, we established 3 plausible categories:

0.9 to 1=optimal elasticity condition
0.75 to 0.9=medium elasticity condition
<0.75=low elasticity condition.

Figure 34:
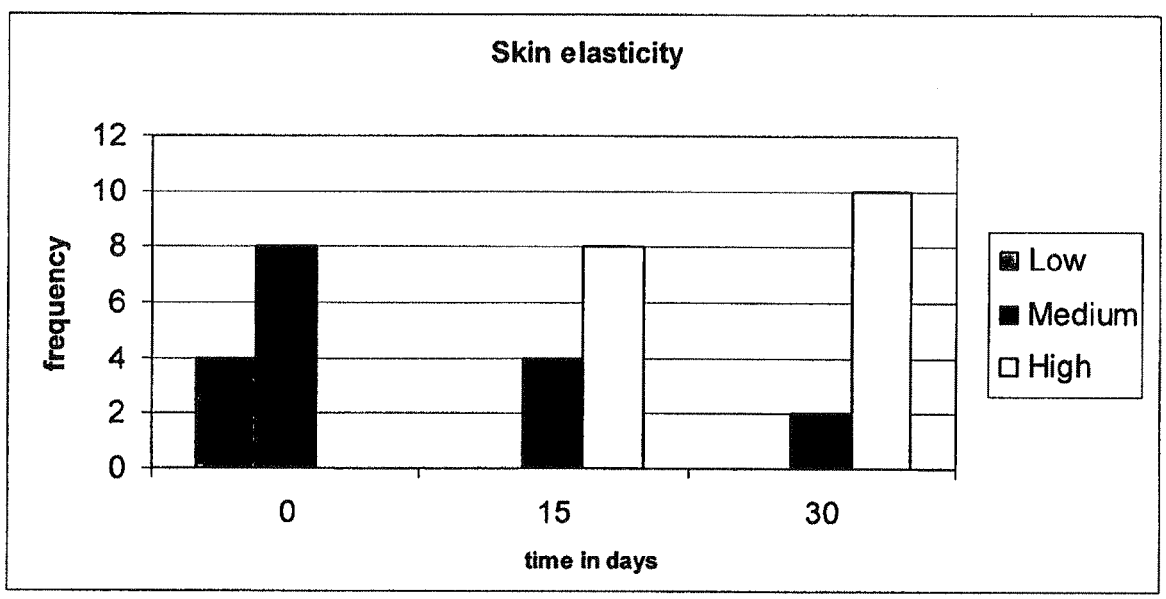
FIG. 34 shows the improvement in skin elasticity obtained during the 30-day period of treatment with a cream containing 8% Basic Extract of AFA Klamath.

Taking into account a 30 days period of treatment, the graph of FIG. 34 reports the level of improvement as the passage of the participants from a lower to a higher level:

Of the 12 participants analyzed, at the beginning 4 had a low elasticity, and 8 a moderate or medium skin elasticity. After 30 days of treatment, there were no more participants with low elasticity; only 2 with medium elasticity, and the remaining 10 had moved up to high elasticity, with an impressive shift from 0 to 10 in this last category!

Skin Moisturization

Figure 35:
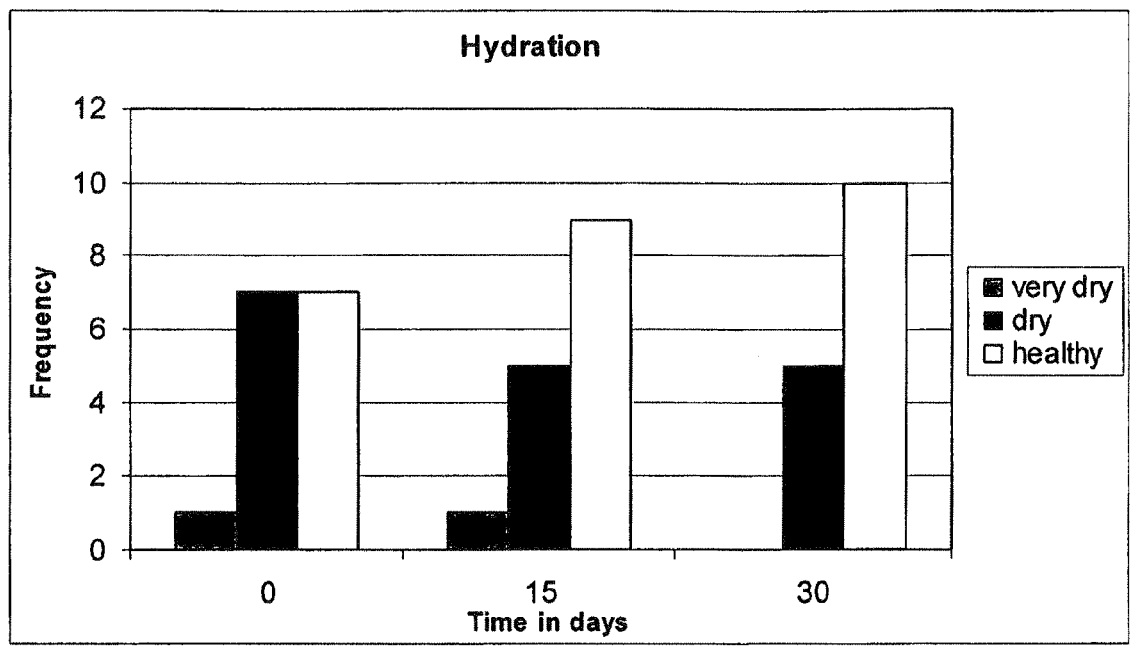
FIG. 35 shows the improvement in skin moisturization obtained during the 30-day period of treatment with a cream containing 8% Basic Extract of AFA Klamath.

A healthy skin in normal room condition (20° C. and 40-60% air humidity) in the tested region should have a moisturizing index >50. Moisturization values in the range 35-50 reveal a moderately dry skin, while the value <35 indicates a very dry skin. Taking these values as our interpretation standard, the graph of FIG. 35 reports the improvement realized in the 30 days period as the passage of the participants from a lower to a higher level:

Of the 15 participants, only 1 (blue color) had a very dry skin; 7 had a moderately dry skin; 7 had a normally moisturized skin. Even though only 8 out of 15 needed a real improvement, the final result shows that at the end of the period of treatment, there were no participants left with a very dry skin; the participants with moderately dry skin were reduced from 7 to 5; while the participants with a healthily moisturized skin moved from 7 to 10.

Skin Profilometry

Figure 36:
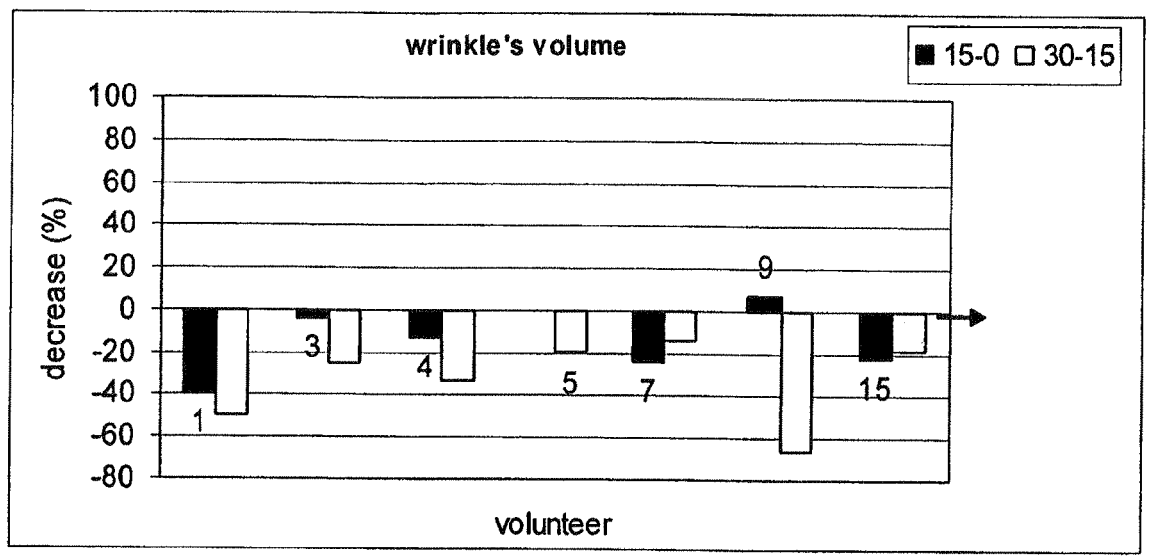
FIG. 36 shows the improvement in volume of skin wrinkles during the 30-day period of treatment with a cream containing 8% Basic Extract of AFA Klamath.

As to the skin profilometry, some of the parameters tested were not usable because too many of the participants had initial or T0 values close to nothing. That is, when we looked at the Ser or akin roughness parameter, we saw that 12 out of 15 participants had an initial value of 0.0 or no skin roughness at all; and in relation to the parameter SEsc or skin scaliness, 10 out of 15 participants had a value of 0.0 or no scaliness at all. Therefore, we limited our evaluation to the two parameters of Sew, or number and width of wrinkles, and VOL, referring to the volume of the wrinkles measured in terms of the wrinkles' depth. Even here, since only 7 participants for the Sew and 9 for the VOL had initial values in need of correction, the remaining having values close to zero, we could not reach statistical significance. Nevertheless, the participants that had even slightly altered values had significant improvements, as shown by FIG. 36.

Thus, in terms of reduction of the volume or depth of the wrinkles, we have a range of decrease in the 30 days period of treatment from −18% to −65%, a very significant level of achievement in terms of wrinkle's volume improvement.

Figure 37:
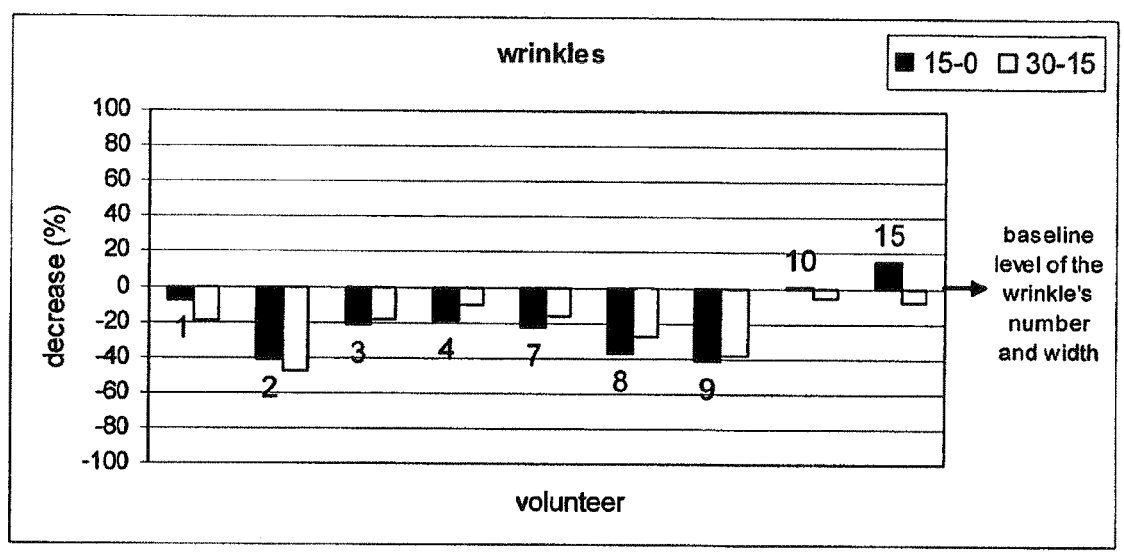
FIG. 37 shows a reduction in the number and width of skin wrinkles obtained during the 30-day period of treatment with a cream containing 8% Basic Extract of AFA Klamath.

In FIG. 37, there is a reduction of the wrinkles number and width in the 30 days period of treatment that goes from −5% to −48%, again a significant result which justifies the claim of the potential efficacy of the AFA extract based cosmetic cream on wrinkles, and most of all that warrants the realization of more specific studies on wrinkles reduction, by selecting participants more specifically affected by this problem.

Bibliography

1. Glazer A. N., *Phycobilisomes, in Methods Enzymol* 1988, 167;304-312.
2. Hirata T., et al., *Antioxidant activities of phycocyanobilin prepared from Spirulina platensis*, in *J Appl Phycol* 2000, 12:435-439.
3. Fuglistaller P., et al., *Isolation and characterization of phycoerythrocyanin and chromatic adaptation of the thermophilic cyanobacterium Mastigocladus laminosus*, in *Arch Microbiol* 1981, 129:268-274.somes, in *Methods Enzymol* 1988, 167;304-312.
5. Suh H J et al., *Mycosporine glycine protects biological systems against photodynamic damage by quenching singlet oxygen with a high efficiency, in Photochem Photobiol*. August 2003;78(2): 109-13.
6. Groniger A et al., *Photoprotective compounds in cyanobacteria, phytoplankton and macroalgae—a database*, in *J Photochem Photobiol B*. November 2000; 58(2-3):115-22.
7. Sinha R P et al., *Induction of mycosporine-like amino acids (MAAs) in cyanobacteria by solar ultraviolet-B radiation*, in *J Photochem Photobiol B*. July 2001; 60(2-3):129-35.
8. Garcia-Pichel F et al., *Occurrence of UV-Absorbing, Mycosporine-Like Compounds among Cyanobacterial Isolates and an Estimate of Their Screening Capacity*, in *Appl Environ Microbiol*. January 1993;59(1):163-169.
9. Kumar S S. et al., *Scavenging of reactive oxygen species by chlorophyllin: an ESR study*, in *Free Radic Res*. November 2001; 35(5):563-74; Kamat J P. et al., *Chlorophyllin as an effective antioxidant against membrane damage in vitro and ex vivo*, in *Biochim Biophys Acta* Sep. 27, 2000;1487 (2-3): 113-27.
10. Ding X W. et al., *CHL prevent colon neoplasm in mice and its selective inhibition on COX-2*, in *Ai Zheng*. November 2004; 23(11 Suppl):1409-13.
11. Fahey J W, *Chlorophyll, chlorophyllin and related tetrapyrroles are significant inducers of mammalian phase 2 cytoprotective genes*. in *Carcinogenesis*. July 2005;26(7): 1247-55; Negishi T. et al., *Antigenotoxic activity of natural chlorophylls*, in *Mutat Res*. May 12, 1997;376(1-2):97-100.
12. Kensler T W, *Chemoprevention of hepatocellular carcinoma in aflatoxin endemic areas*, in *Gastroenterology*. November 2004;127(5 Suppl 1):S310-8.

13. Chiu L C. et al., *The chlorophyllin-induced cell cycle arrest and apoptosis in human breast cancer MCF-7 cells is associated with ERK deactivation and Cyclin D1 depletion*, in *Int J Mol Med*. October 2005;16(4):735-40; Chiu L C., *Antiproliferative effect of chlorophyllin derived from a traditional Chinese medicine Bombyx mori excreta on human breast cancer MCF-7 cells*, in *Int J Oncol*. September 2003;23(3):729-35.
14. G. Dario Diaz et al., *Caspase-8 and Apoptosis-inducing Factor Mediate a Cytochrome c-independent Pathway of Apoptosis in Human Colon Cancer Cells Induced by the Dietary Phytochemical Chlorophyllin*, in *Cancer Research* 63, 1254-1261, Mar. 15, 2003.
15. Blum C A. et al., *Promotion versus suppression of rat colon carcinogenesis by chlorophyllin and chlorophyll: modulation of apoptosis, cell proliferation, and beta-catenin/Tcf signaling*, in *Mutat Res*. February-March 2003; 523-524:217-231.
16. Simon D., Helliwell S., *Extraction and quantification of Chlorophyll A from freshwater green algae*, in *Water Research*, Vol. 32, No 7, pp. 2220-2223, 1998.
17. Porra R., *The chequered history of the development and use of simultaneous equations for the accurate determination of chlorophylls a and b.*, in *Photosynthesis Research* 73: 149-156, 2002.
18. Seddon et al., *Dietary carotenoids, vitamins A, C and E, and Advanced Age-Related Macular Degeneration*, in *JAMA*, 1994; 272: 1413-20; Sobeck U. et al., *Determination of vitamin A palmitate in buccal mucosal cells: a pilot study*, in *Eur J Med Res*. Jun. 28, 2002;7(6):287-9; Rinaldi P. et al., *Plasma antioxidants are similarly depleted in mild cognitive impairment and in Alzheimer's disease*, in *Neurobiol Aging*. November 2003;24(7):915-9; Lovett-Racke A E, Racke M K., *Retinoic acid promotes the development of Th2-like human myelin basic protein-reactive T cells*, in *Cell Immunol*. January 2002;215(1):54-60.
19. Zhao W, Han Y., *Suppressive effect of carotenoids on the luminol dependent chemiluminescence of the stimulated rat macrophages*, in *Chin Med Sci J*. June 1999;14(2):121-4.
20. Cantrell A. et al., *Singlet oxygen quenching by dietary carotenoids in a model membrane environment*, in *Arch Biochem Biophys*. Apr. 1, 2003;412(1):47-54.
21. Surai A P. et al., *Effect of canthaxanthin content of the maternal diet on the antioxidant system of the developing chick*, in *Br Poult Sci*. September 2003;44(4):612-9.
22. Glazer A. N., *Phycobiliproteins*, in *Methods Enzymol*, 1988, 167: 291-303.
23. Bhat V. B., et al., *C-phycocyanin: a potent peroxyl radical scavenger in vivo and in vitro*, in *Biochem Biophys Res Commun.*, 2000; 275(1):20-25; Romay, C. et al., *Antioxidant and antiinflammatory properties of C-phycocyanin from blue-green algae*, in *Inflamm Res*, January 1998; 47(1): 36-41.
24. Reddy C. M., et al., *Selective Inhibition of cyclooxygenase-2 by C-phycocyanin*, in *Biochem Biophys Res Commun.* 2000; 277(3): 599-603.
25. Gonzales R., et al., *Anti-inflammatory activity of phycocyanin extract in acetic acid induced colitis in rats*, in *Pharmacol Res*, 1999; 39(1): 55-9.
26. Gonzales R., et al., *Anti-inflammatory activity of phycocyanin extract in acetic acid induced colitis in rats*, in *Pharmacol Res*, 1999; 39(1): 55-9.
27. Vadiraja B B. et al., *Hepatoprotective effect of C-phycocyanin protection for carbon tetrachloride and R-(+)-pulegone-mediated hepatotoxicty in rats*, in *Biochem Biophys Res Commun*, 1998; 249(2): 428-31.
28. Romay C., et al., *Phycocyanin extract reduces leukotriene B4 levels in arachidonic induced mouse-ear inflammation test*, in *J Pharm Pharmacol*. 1999,51 (5):641-42.
29. Rimbau V., et al., *Protective effects of C-phycocyanin against kainic acid-induced neuronal damage in rat hippocampus*, in *Neurosci Lett* 1999, 276(2): 75-8.
30. Rimbau V., et al., *C-phycocyanin protects cerebellar granule cells from low potassium/serum deprivation-induced apoptosis*, in *Naunyn Schmiedebergs Arch Pharmacol* 2001; 364(2): 96-104.
31. Prior R.L., et al., *Standardized methods for the determination of antioxidant capacity and phenolics in foods and dietary supplements*, in *J Agric Food Chem.* 2005; 53(10): 4290-302.
32. Ou B., et al., *Development and validation of an improved oxygen radical absorbance capacity assay using fluorescine as the fluorescent probe*, in *J Agric Food Chem.* 2001; 49(10): 4619-26.
33. Hsew, Y.C., et al., *Protection of oxidate damage by aqueous extract from Antrodia camphorata mycelia in normal human erthrocytes*, in *Life Sciences* 71(4), 469-482.
34. Bendetti S., et al., *Oxidative stress and antioxidant status in patients undergoing prolonged exposure to hyperbaric oxygen*, in *Clin. Biochem.* 2004; 37(4): 312-7.
35. Reddy C.M. et al., *Selective inhibition of cyclooxygenase-2 by C-phycocyanin, a biliprotein from Spirulina platensis*, in *Biochem Biophys Res Commun* 277(3): 599-603, 2000.
36. Romay C. et al., *Effects of phycocyanin extract on prostaglandin E2 levels in mouse ear inflammation test*, in *Drug Res* 50(2): 1106-1109, 2000.
37. For the comparison of the COX-2 inhibiton produced by the phycocyanins of spirulina and by the drugs celecoxib and rofecoxib, see Reddy C.M. et al., *Selective inhibition of cyclooxygenase-2 by C-phycocyanin, a biliprotein from Spirulina platensis*, in *Biochem Biophys Res Commun* 277 (3): 599-603, 2000.

Since a human being has approximately 3.5 liters of blood, 200 .g/ml multiplied by 3.5 give a total quantity of 600-800 mg. Clearly it is a theoretical calculation in need of experimental confirmations, but it is a plausible hypothesis.

39. Subashini J. et al., *Molecular mechanisms in C-Phycocyanin induced apoptosis in human chronic myeloid leukemia cell line-K562*, in *Biochem Pharmacol*. 2004; 68(3): 453-62.
40. Reddy M.C. et al., *C-Phycocyanin, a selective cyclogenase-2 inhibitor, induces apoptosis in lipopolysaccharide-stimulated RAW 264.7 macrophages*, in *Biochem Biophys Res Commun*. 2003, 304(2): 385-92.
41. Romay Ch., Gonzales R., *Phycocyanin is an Antioxidant Protector of Human Erthrocytes Against Lysis by Peroxyl Radicals*, in *J.Pharm.Pharmacol.*(2000)52: 367-8.
42. Benedetti S., et al., *Antioxydant properties of a novel phycocyanin extract from the blue-green alga Aphanizomenon Flos Aquae*, in *Life Sciences*, 75(2004): 2353-2362.
43. Subhashini J, et al., *Molecular mechanisms in C-Phycocyanin induced apoptosis in human chronic myeloid leukemia cell line-K562.*, in *Biochem Pharmacol*. 2004 Aug. 1; 68(3): 453-62.
44. Hughes J. Lamparter T., *Prokaryotes and Phytochrome. The Connection to Chromophores and Signaling*, in *Plant Physiology*, December 1999, Vol. 121, pp. 1059-1068.

The invention claimed is:

1. An aqueous extract of a Klamath microalgae, *Aphanizomenon Flos Aquae Aquae* Ralfs ex Born. & Flah. Var. *flos aquae* (AFA Klamath), obtained by the following steps:

a) harvesting AFA Klamath, freezing the harvested AFA Klamath and thawing it or, if the starting material is dried AFA Klamath powder, diluting the dried AFA Klamath powder in water, and sonicating the diluted AFA Klamath powder to disrupt cells;
b) centrifuging the thawed AFA Klamath or the sonicated AFA Klamath powder to separate supernatant from a precipitate;
c) collecting the supernatant containing the water-soluble components;
d) concentrating the water-soluble components by subjecting the supernatant obtained in step c) to size-exclusion ultrafiltration with a molecular weight cut-off of 30 kDa to obtain a retentate and a filtrate, wherein the retentate is the aqueous extract of AFA Klamath concentrated in the water-soluble components, phycocyanin/phycoerythrocyanin complex (C-PC/PEC), phycoviolobilin and AFA phytochrome.

2. A composition comprising the aqueous extract of AFA Klamath according to claim 1 and an extract of AFA Klamath comprising lipophilic components, wherein the extract of AFA Klamath comprising lipophilic components is obtained by the following steps:
a) harvesting AFA Klamath, freezing the harvested AFA Klamath and thawing it or, if the starting material is dried AFA Klamath powder, diluting the dried AFA Klamath powder in water, and sonicating the diluted AFA Klamath powder to disrupt cells;
b) centrifuging the thawed AFA Klamath or the sonicated AFA Klamath powder to separate supernatant from a precipitate;
c) drying the precipitate obtained in step b), suspending and homogenizing the dried precipitate in pure ethanol to obtain a suspension;
d) centrifuging the suspension to obtain a pellet and supernatant;
e) collecting the supernatant;
f) optionally, subjecting the pellet to a second ethanol extraction according to steps c) through e);
l) drying the supernatant to obtain the extract of AFA Klamath comprising lipophilic components.

3. A nutritional, cosmetic or pharmaceutical composition comprising the extract of the AFA Klamath microalgae according to claim 1 and a nutritionally, cosmetically or pharmaceutically acceptable excipient.

4. The composition according to claim 3, further containing chlorophyll, beta-carotene, pro-vitamin A carotenoids, xantophyllic carotenes, canthaxanthin, vitamins or minerals.

5. The composition according to claim 3, wherein the composition is in the form of a liquid eyewash.

6. A composition comprising the filtrate obtained in step d) of claim 1 and an extract of AFA Klamath comprising lipophilic components, wherein the extract of AFA Klamath comprising lipophilic components is obtained by the following steps:
i) harvesting AFA Klamath, freezing the harvested AFA Klamath and thawing it or, if the starting material is dried AFA Klamath powder, diluting the dried AFA Klamath powder in water, and sonicating the diluted AFA Klamath powder to disrupt cells;
ii) centrifuging the thawed AFA Klamath or the sonicated AFA Klamath powder to separate supernatant from a precipitate;
iii) drying the precipitate obtained in step ii), suspending and homogenizing the dried precipitate in pure ethanol to obtain a suspension;
iv) centrifuging the suspension to obtain a pellet and supernatant;
v) collecting the supernatant;
vi) optionally, subjecting the pellet to a second ethanol extraction according to steps iii) through v);
vii) drying the supernatant to obtain the extract of AFA Klamath comprising lipophilic components.

7. A method for reducing the occurrence of, controlling or treating oxidative damage to cells or tissues in a subject, comprising administering the extract of AFA Klamath according to claim 1 to the subject.

8. The method according to claim 7, wherein the oxidative damage is caused by hyperbaric treatment.

9. The method according to claim 7, wherein the subject is a human subject.

10. A method for reducing the occurrence of, controlling or treating inflammation in a subject comprising administering the extract of AFA Klamath according to claim 1 to a subject in need thereof.

* * * * *